(12) United States Patent
Andrews et al.

(10) Patent No.: US 6,686,159 B2
(45) Date of Patent: Feb. 3, 2004

(54) METHODS AND COMPOSITIONS FOR MODULATING TELOMERASE REVERSE TRANSCRIPTASE (TERT) EXPRESSION

(75) Inventors: William H. Andrews, Reno, NV (US); Christopher A. Foster, Carmichael, CA (US); Stephanie Fraser, Sparks, NV (US); Hamid Mohammadpour, Reno, NV (US)

(73) Assignee: Sierra Sciences, Inc., Reno, NV (US)

( * ) Notice: Subject to any disclaimer, the term of this patent is extended or adjusted under 35 U.S.C. 154(b) by 43 days.

(21) Appl. No.: 09/932,581

(22) Filed: Aug. 17, 2001

(65) Prior Publication Data

US 2003/0050264 A1 Mar. 13, 2003

Related U.S. Application Data

(60) Provisional application No. 60/227,865, filed on Aug. 24, 2000, provisional application No. 60/230,174, filed on Sep. 1, 2000, and provisional application No. 60/238,345, filed on Oct. 5, 2000.

(51) Int. Cl.[7] .......................... C12Q 1/68; C12N 15/63; G01N 33/53
(52) U.S. Cl. ............................ 435/6; 435/4; 435/7.2; 435/7.21; 435/320.1; 435/325
(58) Field of Search ................ 435/320.1, 325, 435/4, 6, 8, 7.21, 7.2; 536/24.1

(56) References Cited

U.S. PATENT DOCUMENTS

| | | | |
|---|---|---|---|
| 5,858,777 A | 1/1999 | Villeponteau et al. | 435/325 |
| 5,958,680 A | 9/1999 | Villeponteau et al. | 435/6 |
| 6,007,989 A | 12/1999 | West et al. | 435/6 |
| 6,054,575 A | 4/2000 | Villeponteau et al. | 536/24.31 |
| 6,093,809 A | 7/2000 | Cech et al. | 536/23.5 |
| 6,610,839 B1 * | 8/2003 | Morin et al. | 536/24.1 |

FOREIGN PATENT DOCUMENTS

| | | |
|---|---|---|
| WO | WO 99/33998 | 7/1999 |
| WO | WO 99/35243 | 7/1999 |

OTHER PUBLICATIONS

Cong et al., Hum. Mol. Genet. (1999) 8:137–142.
Crowe et al., Biochim Biophys Acta (Mar. 19, 2001) 1518:1–6.
Crowe et al., Nucleic Acids Res. (Jul. 1, 2001) 29:2789–2794.
Henderson et al., Head Neck (Jul. 2000) 22:347–354.
Kim et al., Oncogene (May 10, 2001) 20:2671–82.
Takakura et al., Cancer Res. (1999) 59:551–7.
Yasui et al., J. Gastroenterol. (2000) 35 Suppl. 12: 111–115.
Genbank Accession No. AF114847, Sep. 21, 2000.
Genbank Accession No. AF128893, May 13, 1999.
M. Wick et al. "Genomic organization and promoter characterization of the gene encoding the human telomerase reverse transcriptase (hTERT)" *Gene* 1999, vol. 232, pp 97–109.
I. Horikawa et al. "Cloning and Characterization of the Promoter Region of Human Telomerase Reverse Transcriptase Gene" *Cancer Research*, Feb. 15, 1999, vol. 59, pp826–830.

* cited by examiner

*Primary Examiner*—Ram R. Shukla
(74) *Attorney, Agent, or Firm*—Bret E. Field; Bozicevic, Field & Francis

(57) ABSTRACT

Methods and compositions are provided for modulating, and generally upregulating, the expression of telomerase reverse transcriptase (TERT) by blocking repression of TERT transcription, e.g., by inhibiting binding of repressor factor to a Site C repressor binding site located in the TERT minimal promoter. The subject methods and compositions find use in a variety of different applications, including the immortalization of cells, the production of reagents for use in life science research, therapeutic applications; therapeutic agent screening applications; and the like. In further describing the subject invention, the methods and compositions of the invention are described first in greater detail, followed by a review of the various applications in which the subject invention finds use.

17 Claims, 8 Drawing Sheets

Figure 1

```
     -258        -250        -240        -230        -220        -210
      |           |           |           |           |           |
      CCAGGACC GCGCTCCCCA CGTGGCGGAG GGACTGGGGA CCCGGGCACC CGTCCTGCCC

-200        -190        -180        -170        -160        -150
 |           |           |           |           |           |
 CTTCACCTTC CAGCTCCGCC TCCTCCGCGC GGACCCCGCC CCGTCCCGAC CCCTCCCGGG

-140        -130        -120        -110        -100         -90
 |           |           |           |           |           |
 TCCCCGGCCC AGCCCCCTCC GGGCCCTCCC AGCCCCTCCC CTTCCTTTCC GCGGCCCCGC

-80         -70         -60         -50         -40         -30
  |           |           |           |           |           |
  CCTCTCCTCG CGGCGCGAGT TTCAGGCAGC GCTGCGTCCT GCTGCGCACG TGGGAAGCCC

-20         -10          -1
  |           |           |
  TGGCCCCGGC CACCCCGCG ATG
```

(SEQ ID NO:24)

Figure 2

```
            10         20         30         40         50         60
    GGTACCGAGC TCTTACGCGT GCTAGCCCGG GCTCGAGCCA GGACCGCGCT CCCCACGTGG 70         80         90        100        110        120
    CGGAGGGACT GGGGACCCGG GCACCCGTCC TGCCCCTTCA CCTTCCAGCT CCGCCTCCTC 130        140        150        160        170        180
    CGCGCGGACC CCGCCCCGTC CCGACCCCTC CCGGGTCCCC GGCCCAGCCC CCTCCGGGCC 190        200        210        220        230        240
    CTCCCAGCCC CTCCCCTTCC TTTCCGCGGC CCCGCCCTCT CCTCGCGGCG CGAGTTTCAG 250        260        270        280        290        300
    GCAGCGCTGC GTCCTGCTGC GCACGTGGGA AGCCCTGGCC CCGGCCACCC CCGCGAATTC 310        320        330        340        350        360
    GCCCACCATG CTGCTGCTGC TGCTGCTGCT GGGCCTGAGG CTACAGCTCT CCCTGGGCAT 370        380        390        400        410        420
    CATCCCAGTT GAGGAGGAGA ACCCGGACTT CTGGAACCGC GAGGCAGCCG AGGCCCTGGG 430        440        450        460        470        480
    TGCCGCCAAG AAGCTGCAGC CTGCACAGAC AGCCGCCAAG AACCTCATCA TCTTCCTGGG 490        500        510        520        530        540
    CGATGGGATG GGGGTGTCTA CGGTGACAGC TGCCAGGATC CTAAAAGGGC AGAAGAAGGA 550        560        570        580        590        600
    CAAACTGGGG CCTGAGATAC CCCTGGCCAT GGACCGCTTC CCATATGTGG CTCTGTCCAA 610        620        630        640        650        660
    GACATACAAT GTAGACAAAC ATGTGCCAGA CAGTGGAGCC ACAGCCACGG CCTACCTGTG 670        680        690        700        710        720
    CGGGGTCAAG GGCAACTTCC AGACCATTGG CTTGAGTGCA GCCGCCCGCT TTAACCAGTG 730        740        750        760        770        780
    CAACACGACA CGCGGCAACG AGGTCATCTC CGTGATGAAT CGGGCCAAGA AAGCAGGGAA 790        800        810        820        830        840
    GTCAGTGGGA GTGGTAACCA CCACACGAGT GCAGCACGCC TCGCCAGCCG GCACCTACGC 850        860        870        880        890        900
    CCACACGGTG AACCGCAACT GGTACTCGGA CGCCGACGTG CCTGCCTCGG CCCGCCAGGA 910        920        930        940        950        960
    GGGGTGCCAG GACATCGCTA CGCAGCTCAT CTCCAACATG GACATTGACG TGATCCTAGG 970        980        990       1000       1010       1020
    TGGAGGCCGA AAGTACATGT TTCGCATGGG AACCCCAGAC CCTGAGTACC CAGATGACTA 1030       1040       1050       1060       1070       1080
    CAGCCAAGGT GGGACCAGGC TGGACGGGAA GAATCTGGTG CAGGAATGGC TGGCGAAGCG 1090       1100       1110       1120       1130       1140
    CCAGGGTGCC CGGTATGTGT GGAACCGCAC TGAGCTCATG CAGGCTTCCC TGGACCCGTC
```

Figure 2 (cont)

```
          1150       1160       1170       1180       1190       1200
     TGTGACCCAT CTCATGGGTC TCTTTGAGCC TGGAGACATG AAATACGAGA TCCACCGAGA 1210       1220       1230       1240       1250       1260
     CTCCACACTG GACCCCTCCC TGATGGAGAT GACAGAGGCT GCCCTGCGCC TGCTGAGCAG 1270       1280       1290       1300       1310       1320
     GAACCCCGC GGCTTCTTCC TCTTCGTGGA GGGTGGTCGC ATCGACCATG GTCATCATGA 1330       1340       1350       1360       1370       1380
     AAGCAGGGCT TACCGGGCAC TGACTGAGAC GATCATGTTC GACGACGCCA TTGAGAGGGC 1390       1400       1410       1420       1430       1440
     GGGCCAGCTC ACCAGCGAGG AGGACACGCT GAGCCTCGTC ACTGCCGACC ACTCCCACGT 1450       1460       1470       1480       1490       1500
     CTTCTCCTTC GGAGGCTACC CCCTGCGAGG GAGCTCCATC TTCGGGCTGG CCCCTGGCAA 1510       1520       1530       1540       1550       1560
     GGCCCGGGAC AGGAAGGCCT ACACGGTCCT CCTATACGGA AACGGTCCAG GCTATGTGCT 1570       1580       1590       1600       1610       1620
     CAAGGACGGC GCCCGGCCGG ATGTTACCGA GAGCGAGAGC GGGAGCCCCG AGTATCGGCA 1630       1640       1650       1660       1670       1680
     GCAGTCAGCA GTGCCCCTGG ACGAAGAGAC CCACGCAGGC GAGGACGTGG CGGTGTTCGC 1690       1700       1710       1720       1730       1740
     GCGCGGCCCG CAGGCGCACC TGGTTCACGG CGTGCAGGAG CAGACCTTCA TAGCGCACGT 1750       1760       1770       1780       1790       1800
     CATGGCCTTC GCCGCCTGCC TGGAGCCCTA CACCGCCTGC GACCTGGCGC CCCCGCCGG 1810       1820       1830       1840       1850       1860
     CACCACCGAC GCCGCGCACC CGGGTTACTC TAGAGTCGGG GCGGCCGGCC GCTTCGAGCA 1870       1880       1890       1900       1910       1920
     GACATGATAA GATACATTGA TGAGTTTGGA CAAACCACAA CTAGAATGCA GTGAAAAAAA 1930       1940       1950       1960       1970       1980
     TGCTTTATTT GTGAAATTTG TGATGCTATT GCTTTATTTG TAACCATTAT AAGCTGCAAT 1990       2000       2010       2020       2030       2040
     AAACAAGTTA ACAACAACAA TTGCATTCAT TTTATGTTTC AGGTTCAGGG GGAGGTGTGG 2050       2060       2070       2080       2090       2100
     GAGGTTTTTT AAAGCAAGTA AAACCTCTAC AAATGTGGTA AAATCGATAA GGATCCGTCG 2110       2120       2130       2140       2150       2160
     ACCGATGCCC TTGAGAGCCT TCAACCCAGT CAGCTCCTTC CGGTGGGCGC GGGGCATGAC 2170       2180       2190       2200       2210       2220
     TATCGTCGCC GCACTTATGA CTGTCTTCTT TATCATGCAA CTCGTAGGAC AGGTGCCGGC 2230       2240       2250       2260       2270       2280
     AGCGCTCTTC CGCTTCCTCG CTCACTGACT CGCTGCGCTC GGTCGTTCGG CTGCGGCGAG 2290       2300       2310       2320       2330       2340
     CGGTATCAGC TCACTCAAAG GCGGTAATAC GGTTATCCAC AGAATCAGGG GATAACGCAG
```

Figure 2 (cont)

```
          2350       2360       2370       2380       2390       2400
     GAAAGAACAT GTGAGCAAAA GGCCAGCAAA AGGCCAGGAA CCGTAAAAAG GCCGCGTTGC 2410       2420       2430       2440       2450       2460
     TGGCGTTTTT CCATAGGCTC CGCCCCCCTG ACGAGCATCA CAAAAATCGA CGCTCAAGTC 2470       2480       2490       2500       2510       2520
     AGAGGTGGCG AAACCCGACA GGACTATAAA GATACCAGGC GTTTCCCCCT GGAAGCTCCC 2530       2540       2550       2560       2570       2580
     TCGTGCGCTC TCCTGTTCCG ACCCTGCCGC TTACCGGATA CCTGTCCGCC TTTCTCCCTT 2590       2600       2610       2620       2630       2640
     CGGGAAGCGT GGCGCTTTCT CATAGCTCAC GCTGTAGGTA TCTCAGTTCG GTGTAGGTCG 2650       2660       2670       2680       2690       2700
     TTCGCTCCAA GCTGGGCTGT GTGCACGAAC CCCCCGTTCA GCCCGACCGC TGCGCCTTAT 2710       2720       2730       2740       2750       2760
     CCGGTAACTA TCGTCTTGAG TCCAACCCGG TAAGACACGA CTTATCGCCA CTGGCAGCAG 2770       2780       2790       2800       2810       2820
     CCACTGGTAA CAGGATTAGC AGAGCGAGGT ATGTAGGCGG TGCTACAGAG TTCTTGAAGT 2830       2840       2850       2860       2870       2880
     GGTGGCCTAA CTACGGCTAC ACTAGAAGGA CAGTATTTGG TATCTGCGCT CTGCTGAAGC 2890       2900       2910       2920       2930       2940
     CAGTTACCTT CGGAAAAAGA GTTGGTAGCT CTTGATCCGG CAAACAAACC ACCGCTGGTA 2950       2960       2970       2980       2990       3000
     GCGGTGGTTT TTTTGTTTGC AAGCAGCAGA TTACGCGCAG AAAAAAAGGA TCTCAAGAAG 3010       3020       3030       3040       3050       3060
     ATCCTTTGAT CTTTTCTACG GGGTCTGACG CTCAGTGGAA CGAAAACTCA CGTTAAGGGA 3070       3080       3090       3100       3110       3120
     TTTTGGTCAT GAGATTATCA AAAAGGATCT TCACCTAGAT CCTTTTAAAT TAAAAATGAA 3130       3140       3150       3160       3170       3180
     GTTTTAAATC AATCTAAAGT ATATATGAGT AAACTTGGTC TGACAGTTAC CAATGCTTAA 3190       3200       3210       3220       3230       3240
     TCAGTGAGGC ACCTATCTCA GCGATCTGTC TATTTCGTTC ATCCATAGTT GCCTGACTCC 3250       3260       3270       3280       3290       3300
     CCGTCGTGTA GATAACTACG ATACGGGAGG GCTTACCATC TGGCCCCAGT GCTGCAATGA 3310       3320       3330       3340       3350       3360
     TACCGCGAGA CCCACGCTCA CCGGCTCCAG ATTTATCAGC AATAAACCAG CCAGCCGGAA 3370       3380       3390       3400       3410       3420
     GGGCCGAGCG CAGAAGTGGT CCTGCAACTT TATCCGCCTC CATCCAGTCT ATTAATTGTT 3430       3440       3450       3460       3470       3480
     GCCGGGAAGC TAGAGTAAGT AGTTCGCCAG TTAATAGTTT GCGCAACGTT GTTGCCATTG 3490       3500       3510       3520       3530       3540
     CTACAGGCAT CGTGGTGTCA CGCTCGTCGT TTGGTATGGC TTCATTCAGC TCCGGTTCCC
```

Figure 2 (cont)

```
          3550       3560       3570       3580       3590       3600
     AACGATCAAG GCGAGTTACA TGATCCCCCA TGTTGTGCAA AAAAGCGGTT AGCTCCTTCG 3610       3620       3630       3640       3650       3660
     GTCCTCCGAT CGTTGTCAGA AGTAAGTTGG CCGCAGTGTT ATCACTCATG GTTATGGCAG 3670       3680       3690       3700       3710       3720
     CACTGCATAA TTCTCTTACT GTCATGCCAT CCGTAAGATG CTTTTCTGTG ACTGGTGAGT 3730       3740       3750       3760       3770       3780
     ACTCAACCAA GTCATTCTGA GAATAGTGTA TGCGGCGACC GAGTTGCTCT TGCCCGGCGT 3790       3800       3810       3820       3830       3840
     CAATACGGGA TAATACCGCG CCACATAGCA GAACTTTAAA AGTGCTCATC ATTGGAAAAC 3850       3860       3870       3880       3890       3900
     GTTCTTCGGG GCGAAAACTC TCAAGGATCT TACCGCTGTT GAGATCCAGT TCGATGTAAC 3910       3920       3930       3940       3950       3960
     CCACTCGTGC ACCCAACTGA TCTTCAGCAT CTTTTACTTT CACCAGCGTT CATGAGCAAA 3970       3980       3990       4000       4010       4020
     AACAGGAAGG CAAAATGCCG CAAAAAAGGG AATAAGGGCG ACACGGAAAT GTTGAATACT 4030       4040       4050       4060       4070       4080
     CATACTCTTC CTTTTTCAAT ATTATTGAAG CATTTATCAG GGTTATTGTC TCATGAGCGG 4090       4100       4110       4120       4130       4140
     ATACATATTT GAATGTATTT AGAAAAATAA ACAAATAGGG GTTCCGCGCA CATTTCCCCG 4150       4160       4170       4180       4190       4200
     AAAAGTGCCA CCTGACGTCT AAGAAACCAT TATTATCATG ACATTAACCT ATAAAAATAG 4210       4220       4230       4240       4250       4260
     GCGTATCACG AGGCCCTTTC GTCTCGCGCG TTTCGGTGAT GACGGTGAAA ACCTCTGACA 4270       4280       4290       4300       4310       4320
     CATGCAGCTC CCGGAGACGG TCACAGCTTG TCTGTAAGCG GATGCCGGGA GCAGACAAGC 4330       4340       4350       4360       4370       4380
     CCGTCAGGGC GCGTCAGCGG GTGTTGGCGG GTGTCGGGGC TGGCTTAACT ATGCGGCATC 4390       4400       4410       4420       4430       4440
     AGAGCAGATT GTACTGAGAG TGCACCATAT GCGGTGTGAA TCTCGTACGC ACGTGCCTCA 4450       4460       4470       4480       4490       4500
     GTACGTAAGA GGTTCCAACT TTCACCATAA TGAAATAAGA TCACTACCGG GCGTATTTTT 4510       4520       4530       4540       4550       4560
     TGAGTTATCG AGATTTTCAG GAGCTAAGGA AGCTAAAATG GAGAAAAAAA TCACTGGATA 4570       4580       4590       4600       4610       4620
     TACCACCGTT GATATATCCC AATGGCATCG TAAAGAACAT TTGAGGCAT TTCAGTCAGT 4630       4640       4650       4660       4670       4680
     TGCTCAATGT ACCTATAACC AGACCGTTCA ACTGGATATT ACGGCCTTTT TAAAGACCGT 4690       4700       4710       4720       4730       4740
     AAAGAAAAAT AAGCACAAGT TTTATCCGGC CTTTATTCAC ATTCTTGCCC GCCTGATGAA
```

Figure 2 (cont)

```
           4750       4760       4770       4780       4790       4800
      TGCTCATCCC GAGTTCCGTA TGGCAATGAA AGACGGTGAG CTGGTGATAT GGGATAGTGT 4810       4820       4830       4840       4850       4860
      TCACCCTTGT TACACCGTTT TCCATGAGCA AACTGAAACG TTTTCATCGC TCTGGAGTGA 4870       4880       4890       4900       4910       4920
      ATACCACGAC GATTTCCGGC AGTTTCTACA CATATATTCG CAAGATGTGG CGTGTTACGG 4930       4940       4950       4960       4970       4980
      TGAAAACCTG GCCTATTTCC CTAAAGGGTT TATTGAGAAT ATGTTTTTCG TCTCAGCCAA 4990       5000       5010       5020       5030       5040
      TCCCTGGGTG AGTTTCACCA GTTTTGATTT AAACGTGGCC AATATGGACA ACTTCTTCGC 5050       5060       5070       5080       5090       5100
      CCCCGTTTTC ACAATGGGCA AATATTATAC GCAAGGCGAC AAGGTGCTGA TGCCGCTGGC 5110       5120       5130       5140       5150       5160
      GATTCAGGTT CATCATGCCG TTTGTGATGG CTTCCATGTC GGCAGAATGC TTAATGAATT 5170       5180       5190       5200       5210       5220
      ACAACAGTGT ACCGCATCAG GCGAAATTGT AAACGTTAAT ATTTGTTAA AATTCGCGTA 5230       5240       5250       5260       5270       5280
      AATATTTGTT AAATCAGCTC ATTTTTTAAC CAATAGGCCG AAATCGGCAA AATCCCTTAT 5290       5300       5310       5320       5330       5340
      AAATCAAAAG AATAGACCGA GATAGGGTTG AGTGTTGTTC CAGTTTGGAA CAAGAGTCCA 5350       5360       5370       5380       5390       5400
      CTATTAAAGA ACGTGGACTC CAACGTCAAA GGGCGAAAAA CCGTCTATCA GGGCGATGGC 5410       5420       5430       5440       5450       5460
      CCACTACGTG AACCATCACC CAAATCAAGT TTTTTGCGGT CGAGGTGCCG TAAAGCTCTA 5470       5480       5490       5500       5510       5520
      AATCGGAACC CTAAAGGGAG CCCCCGATTT AGAGCTTGAC GGGGAAAGCC GGCGAACGTG 5530       5540       5550       5560       5570       5580
      GCGAGAAAGG AAGGGAAGAA AGCGAAAGGA GCGGGCGCTA GGGCGCTGGC AAGTGTAGCG 5590       5600       5610       5620       5630       5640
      GTCACGCTGC GCGTAACCAC CACACCCGCC GCGCTTAATG CGCCGCTACA GGGCGCGTCC 5650       5660       5670       5680       5690       5700
      ATTCGCCATT CAGGCTGCGC AACTGTTGGG AAGGGCGATC GGTGCGGGCC TCTTCGCTAT 5710       5720       5730       5740       5750       5760
      TACGCCAGCC CAAGCTACCA TGATAAGTAA GTAATATTAA GGTACGGGAG GTACTTGGAG 5770       5780       5790       5800       5810       5820
      CGGCCGCAAT AAAATATCTT TATTTTCATT ACATCTGTGT GTTGGTTTTT TGTGTGAATC 5830       5840       5850       5860       5870       5880
      GATAGTACTA ACATACGCTC TCCATCAAAA CAAAACGAAA CAAAACAAAC TAGCAAAATA 5890       5900       5910       5920       5928
      GGCTGTCCCC AGTGCAAGTG CAGGTGCCAG AACATTTCTC TATCGATA (SEQ ID NO:25)
```

Figure 2 (cont)

annotations:

| START | END | DIRECTION | DESCRIPTION |
|-------|-----|-----------|-------------|
| 38 | 295 | -> | Telomerase Minimal Promoter. |
| 295 | 310 | -> | EcoRI site and Kozak Sequence. |
| 308 | 1864 | -> | Secreted Alkaline Phosphotase Gene. |
| 1860 | 2080 | -> | Late Poly-A addition site of SV40. |
| 2394 | 2976 | | Bacterial Origin of Replication. |
| 3170 | 4023 | <- | Ampillicin Resistance Gene Made Sensitive by Mutagenesis. |
| 4538 | 5196 | -> | Chloramphenicol Resistance Gene. |
| 5217 | 5401 | <- | F1 Origin of Replication. |
| 5768 | 5921 | -> | Transcription blocker. |

```
                         SEQUENCE LISTING

<160> NUMBER OF SEQ ID NOS: 25

<210> SEQ ID NO 1
<211> LENGTH: 41
<212> TYPE: DNA
<213> ORGANISM: human

<400> SEQUENCE: 1
ggccccgccc tctcctcgcg gcgcgagttt caggcagcgc t                    41

<210> SEQ ID NO 2
<211> LENGTH: 13
<212> TYPE: DNA
<213> ORGANISM: human

<400> SEQUENCE: 2
ggcgcgagtt tca                                                   13

<210> SEQ ID NO 3
<211> LENGTH: 10
<212> TYPE: DNA
<213> ORGANISM: human

<400> SEQUENCE: 3
cgcgagtttc                                                       10

<210> SEQ ID NO 4
<211> LENGTH: 21
<212> TYPE: DNA
<213> ORGANISM: human

<400> SEQUENCE: 4
ggcgcgagtt tcaggcagcg c                                          21

<210> SEQ ID NO 5
<211> LENGTH: 85
<212> TYPE: PRT
<213> ORGANISM: human

<400> SEQUENCE: 5

Gly Arg Gly Arg His Pro Gly Lys Gly Val Lys Ser Pro Gly Glu Lys
 1               5                  10                  15

Ser Arg Tyr Glu Thr Ser Leu Asn Leu Thr Thr Lys Arg Phe Leu Glu
                20                  25                  30

Leu Leu Ser His Ser Ala Asp Gly Val Val Asp Leu Asn Trp Ala Ala
            35                  40                  45

Glu Val Leu Lys Val Gln Lys Arg Arg Ile Tyr Asp Ile Thr Asn Val
        50                  55                  60

Leu Glu Gly Ile Gln Leu Ile Ala Lys Lys Ser Lys Asn His Ile Gln
 65                  70                  75                  80

Trp Leu Gly Ser His
                85

<210> SEQ ID NO 6
<211> LENGTH: 76
<212> TYPE: PRT
<213> ORGANISM: human
```

<400> SEQUENCE: 6

| Pro | Pro | Gly | Thr | Pro | Ser | Arg | His | Glu | Lys | Ser | Leu | Gly | Leu | Leu | Thr |
|---|---|---|---|---|---|---|---|---|---|---|---|---|---|---|---|
| 1 | | | | 5 | | | | | 10 | | | | | 15 | |

| Thr | Lys | Phe | Val | Ser | Leu | Leu | Gln | Glu | Ala | Lys | Asp | Gly | Val | Leu | Asp |
|---|---|---|---|---|---|---|---|---|---|---|---|---|---|---|---|
| | | | 20 | | | | | 25 | | | | | 30 | | |

| Leu | Lys | Leu | Ala | Ala | Asp | Thr | Leu | Ala | Val | Arg | Gln | Lys | Arg | Arg | Ile |
|---|---|---|---|---|---|---|---|---|---|---|---|---|---|---|---|
| | 35 | | | | | 40 | | | | | 45 | | | | |

| Tyr | Asp | Ile | Thr | Asn | Val | Leu | Glu | Gly | Ile | Leu | Ile | Glu | Lys | Lys |
|---|---|---|---|---|---|---|---|---|---|---|---|---|---|---|
| 50 | | | | | 55 | | | | | 60 | | | | |

| Ser | Lys | Asn | Ser | Ile | Gln | Trp | Lys | Gly | Val | Gly | Pro |
|---|---|---|---|---|---|---|---|---|---|---|---|
| 65 | | | | | 70 | | | | 75 | | |

<210> SEQ ID NO 7
<211> LENGTH: 78
<212> TYPE: DNA
<213> ORGANISM: human

<400> SEQUENCE: 7
ctcctcgcgg cgcgagtttc aggcagcgct gcgtcctgct gcgcacgtgg gaagccctgg      60
ccccggccac ccccgcga                                                    78

<210> SEQ ID NO 8
<211> LENGTH: 10
<212> TYPE: DNA
<213> ORGANISM: human

<400> SEQUENCE: 8
cgcgagtttc                                                             10

<210> SEQ ID NO 9
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 9
tctcctcgcg gcgcgagttt cagg                                             24

<210> SEQ ID NO 10
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 10
tctcctcgcg gcgcgagttt caggca                                           26

<210> SEQ ID NO 11
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 11
tctcctcgcg gcgcgagttt caggcagc                                         28

<210> SEQ ID NO 12
<211> LENGTH: 29

<212> TYPE: DNA
<213> ORGANISM: Artificial Sequence
<220> FEATURE:
<223> OTHER INFORMATION: synthetic oligonucleotide

<400> SEQUENCE: 12
tctcctcgcg gcgcgagttt caggcagcg                              29

<210> SEQ ID NO 13
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 13
tctcctcgcg gcgcgagttt caggcagcgc                             30

<210> SEQ ID NO 14
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 14
ctcgcggcgc gagtttcagg cagcgctg                               28

<210> SEQ ID NO 15
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 15
tctcctcgcg gcgcgagttt caggcagcgc                             30

<210> SEQ ID NO 16
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 16
tcctcgcggc gcgagtttca ggcagcgc                               28

<210> SEQ ID NO 17
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 17
ctcgcggcgc gagtttcagg cagcgc                                 26

<210> SEQ ID NO 18
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 18

<210> SEQ ID NO 19
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 19
cggcgcgagt tcaggcagc gctgcgtc                                28

<210> SEQ ID NO 20
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 20
gcgcgagttt caggcagcgc tgcgtc                                 26

<210> SEQ ID NO 21
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 21
cgcgagtttc aggcagcgct gcgtc                                  25

<210> SEQ ID NO 22
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 22
gcgagtttca ggcagcgctg cgtc                                   24

<210> SEQ ID NO 23
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 23
tctcctcgcg gcgagagttt caggcagcgc                             30

<210> SEQ ID NO 24
<211> LENGTH: 261
<212> TYPE: DNA
<213> ORGANISM: human

<400> SEQUENCE: 24
ccaggaccgc gctccccacg tggcggaggg actggggacc cgggcacccg tcctgcccct    60
tcaccttcca gctccgcctc ctccgcgcgg accccgcccc gtcccgaccc ctcccgggtc   120
cccggcccag cccctccgg gcctccag cccctccct tcctttccgc ggccccgccc      180
tctcctcgcg gcgcgagttt caggcagcgc tgcgtcctgc tgcgcacgtg ggaagccctg   240
gccccggcca ccccgcgat g                                              261

<210> SEQ ID NO 25
<211> LENGTH: 5928
<212> TYPE: DNA
<213> ORGANISM: Artificial Sequence
<220> FEATURE:
<223> OTHER INFORMATION: synthetic expression plasmid

<400> SEQUENCE: 25

| | | | | | |
|---|---|---|---|---|---|
| ggtaccgagc | tcttacgcgt | gctagcccgg | gctcgagcca | ggaccgcgct | ccccacgtgg | 60 |
| cggagggact | ggggacccgg | gcacccgtcc | tgccccttca | ccttccagct | ccgcctcctc | 120 |
| cgcgcggacc | ccgccccgtc | ccgacccctc | ccgggtcccc | ggcccagccc | ctccgggcc | 180 |
| ctcccagccc | ctccccttcc | tttccgcggc | cccgccctct | cctcgcggcg | cgagtttcag | 240 |
| gcagcgctgc | gtcctgctgc | gcacgtggga | agccctggcc | ccggccaccc | ccgcgaattc | 300 |
| gcccaccatg | ctgctgctgc | tgctgctgct | gggcctgagg | ctacagctct | ccctgggcat | 360 |
| catcccagtt | gaggaggaga | acccggactt | ctggaaccgc | gaggcagccg | aggccctggg | 420 |
| tgccgccaag | aagctgcagc | ctgcacagac | agccgccaag | aacctcatca | tcttcctggg | 480 |
| cgatgggatg | ggggtgtcta | cggtgacagc | tgccaggatc | ctaaaagggc | agaagaagga | 540 |
| caaactgggg | cctgagatac | ccctggccat | ggaccgcttc | ccatatgtgg | ctctgtccaa | 600 |
| gacatacaat | gtagacaaac | atgtgccaga | cagtggagcc | acagccacgg | cctacctgtg | 660 |
| cggggtcaag | ggcaacttcc | agaccattgg | cttgagtgca | gccgcccgct | taaccagtg | 720 |
| caacacgaca | cgcggcaacg | aggtcatctc | cgtgatgaat | cgggccaaga | aagcagggaa | 780 |
| gtcagtggga | gtggtaacca | ccacacgagt | gcagcacgcc | tcgccagccg | gcacctacgc | 840 |
| ccacacggtg | aaccgcaact | ggtactcgga | cgccgacgtg | cctgcctcgg | cccgccagga | 900 |
| ggggtgccag | gacatcgcta | cgcagctcat | ctccaacatg | gacattgacg | tgatcctagg | 960 |
| tggaggccga | agtacatgt | tcgcatggg | aaccccagac | cctgagtacc | cagatgacta | 1020 |
| cagccaaggt | gggaccaggc | tggacgggaa | gaatctggtg | caggaatggc | tggcgaagcg | 1080 |
| ccagggtgcc | cggtatgtgt | ggaaccgcac | tgagctcatg | caggcttccc | tggacccgtc | 1140 |
| tgtgacccat | ctcatgggtc | tctttgagcc | tggagacatg | aaatacgaga | tccaccgaga | 1200 |
| ctccacactg | gaccccctcc | tgatggagat | gacagaggct | gccctgcgcc | tgctgagcag | 1260 |
| gaacccccgc | ggcttcttcc | tcttcgtgga | gggtggtcgc | atcgaccatg | gtcatcatga | 1320 |
| aagcagggct | taccgggcac | tgactgagac | gatcatgttc | gacgacgcca | ttgagagggc | 1380 |
| gggccagctc | accagcgagg | aggacacgct | gagcctcgtc | actgccgacc | actcccacgt | 1440 |
| cttctccttc | ggaggctacc | ccctgcgagg | gagctccatc | ttcgggctgg | ccctggcaa | 1500 |
| ggccccgggac | aggaaggcct | acacggtcct | cctatacgga | aacggtccag | gctatgtgct | 1560 |
| caaggacggc | gccggccgg | atgttaccga | gagcgagagc | gggagcccg | agtatcggca | 1620 |
| gcagtcagca | gtgcccctgg | acgaagagac | ccacgcaggc | gaggacgtgg | cggtgttcgc | 1680 |
| gcgcggcccg | caggcgcacc | tggttcacgg | cgtgcaggag | cagaccttca | tagcgcacgt | 1740 |
| catggccttc | gccgcctgcc | tggagcccta | caccgcctgc | gacctggcgc | ccccgccgg | 1800 |
| caccaccgac | gccgcgcacc | cgggttactc | tagagtcggg | gcggccggcc | gcttcgagca | 1860 |
| gacatgataa | gatacattga | tgagtttgga | caaaccacaa | ctagaatgca | gtgaaaaaaa | 1920 |
| tgctttattt | gtgaaatttg | tgatgctatt | gctttatttg | taaccattat | aagctgcaat | 1980 |
| aaacaagtta | acaacaacaa | ttgcattcat | tttatgtttc | aggttcaggg | ggaggtgtgg | 2040 |

```
gaggttttt   aaagcaagta   aaacctctac   aaatgtggta   aaatcgataa   ggatccgtcg   2100
accgatgccc   ttgagagcct   tcaacccagt   cagctccttc   cggtgggcgc   ggggcatgac   2160
tatcgtcgcc   gcacttatga   ctgtcttctt   tatcatgcaa   ctcgtaggac   aggtgccggc   2220
agcgctcttc   cgcttcctcg   ctcactgact   cgctgcgctc   ggtcgttcgg   ctgcggcgag   2280
cggtatcagc   tcactcaaag   gcggtaatac   ggttatccac   agaatcaggg   gataacgcag   2340
gaaagaacat   gtgagcaaaa   ggccagcaaa   aggccaggaa   ccgtaaaaag   gccgcgttgc   2400
tggcgttttt   ccataggctc   cgcccccctg   acgagcatca   caaaaatcga   cgctcaagtc   2460
agaggtggcg   aaacccgaca   ggactataaa   gataccaggc   gtttccccct   ggaagctccc   2520
tcgtgcgctc   tcctgttccg   accctgccgc   ttaccggata   cctgtccgcc   tttctccctt   2580
cgggaagcgt   ggcgctttct   catagctcac   gctgtaggta   tctcagttcg   gtgtaggtcg   2640
ttcgctccaa   gctgggctgt   gtgcacgaac   cccccgttca   gcccgaccgc   tgcgccttat   2700
ccggtaacta   tcgtcttgag   tccaacccgg   taagacacga   cttatcgcca   ctggcagcag   2760
ccactggtaa   caggattagc   agagcgaggt   atgtaggcgg   tgctacagag   ttcttgaagt   2820
ggtggcctaa   ctacggctac   actagaagga   cagtatttgg   tatctgcgct   ctgctgaagc   2880
cagttacctt   cggaaaaaga   gttggtagct   cttgatccgg   caaacaaacc   accgctggta   2940
gcggtggttt   ttttgtttgc   aagcagcaga   ttacgcgcag   aaaaaaagga   tctcaagaag   3000
atcctttgat   cttttctacg   gggtctgacg   ctcagtggaa   cgaaaactca   cgttaaggga   3060
ttttggtcat   gagattatca   aaaaggatct   tcacctagat   ccttttaaat   taaaaatgaa   3120
gttttaaatc   aatctaaagt   atatatgagt   aaacttggtc   tgacagttac   caatgcttaa   3180
tcagtgaggc   acctatctca   gcgatctgtc   tatttcgttc   atccatagtt   gcctgactcc   3240
ccgtcgtgta   gataactacg   atacgggagg   gcttaccatc   tggccccagt   gctgcaatga   3300
taccgcgaga   cccacgctca   ccggctccag   atttatcagc   aataaaccag   ccagccggaa   3360
gggccgagcg   cagaagtggt   cctgcaactt   tatccgcctc   catccagtct   attaattgtt   3420
gccgggaagc   tagagtaagt   agttcgccag   ttaatagttt   gcgcaacgtt   gttgccattg   3480
ctacaggcat   cgtggtgtca   cgctcgtcgt   ttggtatggc   ttcattcagc   tccggttccc   3540
aacgatcaag   gcgagttaca   tgatccccca   tgttgtgcaa   aaaagcggtt   agctccttcg   3600
gtcctccgat   cgttgtcaga   agtaagttgg   ccgcagtgtt   atcactcatg   gttatggcag   3660
cactgcataa   ttctcttact   gtcatgccat   ccgtaagatg   cttttctgtg   actggtgagt   3720
actcaaccaa   gtcattctga   gaatagtgta   tgcggcgacc   gagttgctct   tgcccggcgt   3780
caatacggga   taataccgcg   ccacatagca   gaactttaaa   agtgctcatc   attggaaaac   3840
gttcttcggg   gcgaaaactc   tcaaggatct   taccgctgtt   gagatccagt   tcgatgtaac   3900
ccactcgtgc   acccaactga   tcttcagcat   cttttacttt   caccagcgtt   catgagcaaa   3960
aacaggaagg   caaaatgccg   caaaaaaggg   aataagggcg   acacggaaat   gttgaatact   4020
catactcttc   ctttttcaat   attattgaag   catttatcag   ggttattgtc   tcatgagcgg   4080
atacatattt   gaatgtattt   agaaaaataa   acaaataggg   gttccgcgca   catttccccg   4140
aaaagtgcca   cctgacgtct   aagaaaccat   tattatcatg   acattaacct   ataaaaatag   4200
gcgtatcacg   aggccctttc   gtctcgcgcg   tttcggtgat   gacggtgaaa   acctctgaca   4260
catgcagctc   ccggagacgg   tcacagcttg   tctgtaagcg   gatgccggga   gcagacaagc   4320
ccgtcagggc   gcgtcagcgg   gtgttggcgg   gtgtcggggc   tggcttaact   atgcggcatc   4380
agagcagatt   gtactgagag   tgcaccatat   gcggtgtgaa   tctcgtacgc   acgtgcctca   4440
```

-continued

```
gtacgtaaga ggttccaact ttcaccataa tgaaataaga tcactaccgg gcgtattttt      4500
tgagttatcg agattttcag gagctaagga agctaaaatg gagaaaaaaa tcactggata      4560
taccaccgtt gatatatccc aatggcatcg taaagaacat tttgaggcat ttcagtcagt      4620
tgctcaatgt acctataacc agaccgttca actggatatt acggccttt taaagaccgt       4680 aaagaaaaat aagcacaagt tttatccggc ctttattcac attcttgccc gcctgatgaa      4740
tgctcatccc gagttccgta tggcaatgaa agacggtgag ctggtgatat gggatagtgt      4800
tcacccttgt tacaccgttt tccatgagca aactgaaacg ttttcatcgc tctggagtga      4860
ataccacgac gatttccggc agtttctaca catatattcg caagatgtgg cgtgttacgg      4920
tgaaaacctg gcctatttcc ctaaagggtt tattgagaat atgtttttcg tctcagccaa      4980
tccctgggtg agtttcacca gttttgattt aaacgtggcc aatatggaca acttcttcgc      5040
ccccgttttc acaatgggca aatattatac gcaaggcgac aaggtgctga tgccgctggc      5100
gattcaggtt catcatgccg tttgtgatgg cttccatgtc ggcagaatgc ttaatgaatt      5160
acaacagtgt accgcatcag gcgaaattgt aaacgttaat attttgttaa aattcgcgta      5220
aatatttgtt aaatcagctc atttttaac caataggccg aaatcggcaa aatcccttat       5280
aaatcaaaag aatagaccga gatagggttg agtgttgttc cagtttggaa caagagtcca      5340
ctattaaaga acgtggactc caacgtcaaa gggcgaaaaa ccgtctatca gggcgatggc      5400
ccactacgtg aaccatcacc caaatcaagt tttttgcggt cgaggtgccg taaagctcta      5460
aatcggaacc ctaaagggag cccccgattt agagcttgac ggggaaagcc ggcgaacgtg      5520
gcgagaaagg aagggaagaa agcgaaagga gcgggcgcta gggcgctggc aagtgtagcg      5580
gtcacgctgc gcgtaaccac cacacccgcc gcgcttaatg cgccgctaca gggcgcgtcc      5640
attcgccatt caggctgcgc aactgttggg aagggcgatc ggtgcgggcc tcttcgctat      5700
tacgccagcc caagctacca tgataagtaa gtaatattaa ggtacgggag gtacttggag      5760
cggccgcaat aaaatatctt tattttcatt acatctgtgt gttggttttt tgtgtgaatc      5820
gatagtacta acatacgctc tccatcaaaa caaaacgaaa caaaacaaac tagcaaaata      5880
ggctgtcccc agtgcaagtg caggtgccag aacatttctc tatcgata                   5928
```

METHODS AND COMPOSITIONS FOR MODULATING TELOMERASE REVERSE TRANSCRIPTASE (TERT) EXPRESSION

CROSS-REFERENCE TO RELATED APPLICATIONS

Pursuant to 35 U.S.C. § 119 (e), this application claims priority to the filing dates of the United States Provisional Patent Application Ser. Nos. 60/227,865 filed Aug. 24, 2000; 60/230,174 filed Sep. 1, 2000 and 60/238,345 filed Oct. 5, 2000, the disclosures of which are herein incorporated by reference.

INTRODUCTION

1. Field of the Invention

The field of this invention is the telomerase reverse transcriptase gene, specifically the regulation of the expression thereof.

2. Background of the Invention

Telomeres, which define the ends of chromosomes, consist of short, tandemly repeated DNA sequences loosely conserved in eukaryotes. Human telomeres consist of many kilobases of (TTAGGG)n together with various associated proteins. Small amounts of these terminal sequences or telomeric DNA are lost from the tips of the chromosomes during S phase because of incomplete DNA replication. Many human cells progressively lose terminal sequence with cell division, a loss that correlates with the apparent absence of telomerase in these cells. The resulting telomeric shortening has been demonstrated to limit cellular lifespan.

Telomerase is a ribonucleoprotein that synthesizes telomeric DNA. Human telomerase is made up of two components: (1) an essential structural RNA (TER) (where the human component is referred to in the art as hTER); and (2) a catalytic protein (telomerase reverse transcriptase or TERT) (where the human component is referred to in the art as hTERT). Telomerase works by recognizing the 3' end of DNA, e.g., telomeres, and adding multiple telomeric repeats to its 3' end with the catalytic protein component, e.g., hTERT, which has polymerase activity, and hTER which serves as the template for nucleotide incorporation. Of these two components of the telomerase enzyme, both the catalytic protein component and the RNA template component are activity limiting components.

Because of its role in cellular senescence and immortalization, there is much interest in the development of protocols and compositions for regulating expression of telomerase.

Relevant Literature

U.S. Patents of interest include: 6,093,809; 6,054,575; 6,007,989; 5,958,680; 5,858,777. Also of interest are WO 99/33998 and WO 99/35243. Articles of interest include: Cong et al., Hum. Mol. Genet. (1999) 8:137–142; Crowe et al., Nucleic Acids Res. (Jul. 1, 2001) 29:2789–2794; Crowe et al., Biochim Biophys Acta (March 19, 2001) 1518:1–6; Henderson et al., Head Neck (July 2000) 22:347–354; Kim et al., Oncogene (May 10, 2001) 20:2671–82; Takakura et al., Cancer Res. (1999) 59:551–7; and Yasui et al., J. Gastroenterol. (2000) 35 Suppl. 12: 111–115. See also GENBANK accession nos. AF1 14847 and 128893.

SUMMARY OF THE INVENTION

Methods and compositions are provided for modulating, and generally upregulating, the expression of telomerase reverse transcriptase (TERT) by blocking repression of TERT transcription, e.g., by inhibiting binding of repressor factor to a Site C repressor binding site located in the TERT minimal promoter, where in certain embodiments the repressor factor acts in concert with one or more cofactors in binding to the Site C repressor site to inhibit the TERT transcription site. The subject methods and compositions find use in a variety of different applications, including the immortalization of cells, the production of reagents for use in life science research, therapeutic applications; therapeutic agent screening applications; and the like.

BRIEF DESCRIPTION OF THE FIGURES.

FIG. 1 provides the sequence of the minimal Tert Promoter referenced in the experimental section, below.

FIG. 2 provides an annotated sequence of the pSS120 plasmid references in the Experimental Section, below.

DESCRIPTION OF THE SPECIFIC EMBODIMENTS

Figure 3:
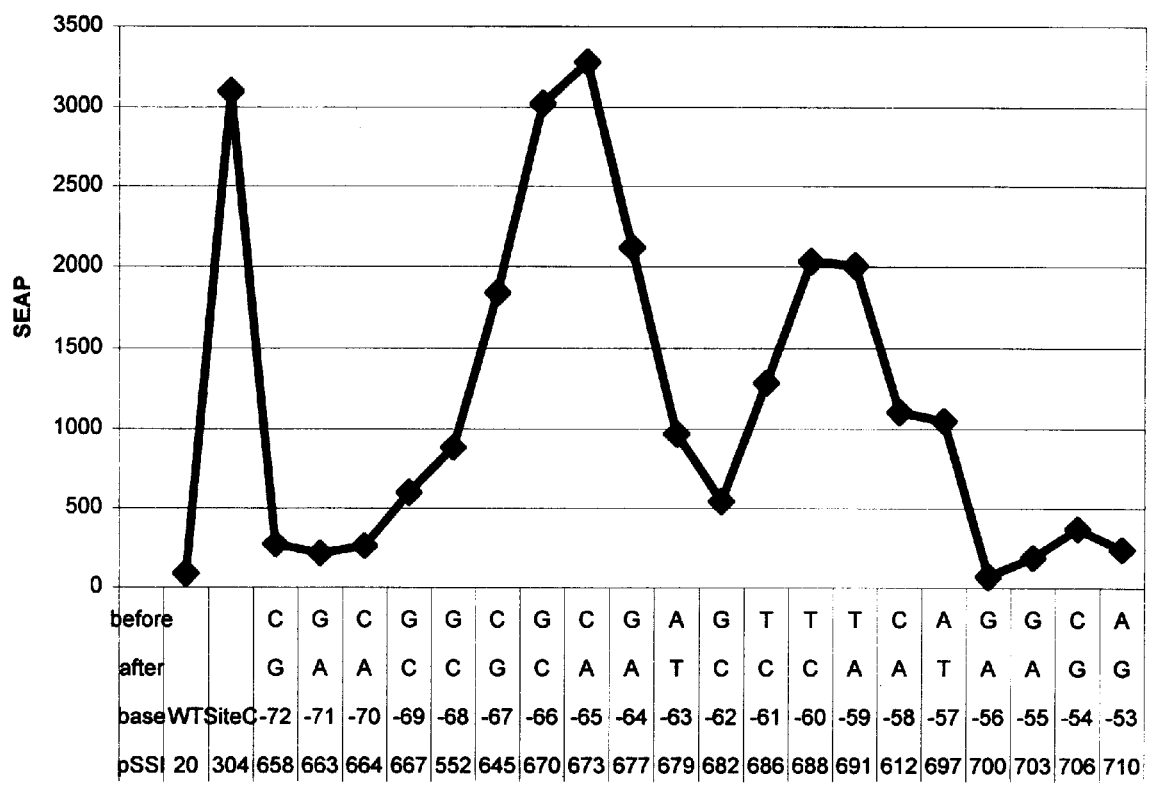
FIG. 3 provides graphical results of the fine mapping analysis experiment reported in the Experimental Section, below.

Methods and compositions are provided for modulating, and generally upregulating, the expression of telomerase reverse transcriptase (TERT) by blocking repression of TERT transcription, e.g., by inhibiting binding of repressor factor to a Site C repressor binding site located in the TERT minimal promoter, where in certain embodiments the repressor factor acts in concert with one or more cofactors in binding to the Site C repressor site to inhibit the TERT transcription site. The subject methods and compositions find use in a variety of different applications, including the immortalization of cells, the production of reagents for use in life science research, therapeutic applications; therapeutic agent screening applications; and the like. In further describing the subject invention, the methods and compositions of the invention are described first in greater detail, followed by a review of the various applications in which the subject invention finds use.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

Methods

As summarized above, the subject invention provides methods and compositions for modulating expression of TERT. In the subject methods, TERT expression repression is modulated by modulating the TERT expression repression activity of a Site C repressor binding site located in the TERT minimal promoter, where modulating includes both increasing and decreasing the expression repressive activity of the Site C repressor binding site. As such, in certain embodiments, methods of increasing expression of TERT are provided, while in other embodiments, methods of decreasing expression of TERT are provided, where in both embodiments the modulation of expression is accomplished by modulating the repressor activity of the Site C repressor site.

Site C Repressor Site

The Site C repressor site whose activity is modulated in the subject methods comprises a sequence of nucleotide residues that is bound by an E2F protein, or at least an E2F DNA binding domain of an E2F protein. E2F proteins to which the subject Site C repressor site binds include, but are not limited to: E2F-1, E2F-2, E2F-3, E2F-4, E2F-5 and E2F-6.

The target Site C repressor site typically ranges in length from about 1 base, usually at least about 5 bases and more usually at least about 15 bases, to a length of about 25 bases or longer, e.g., 50, 75 or 100, etc. In many embodiments, the length of the target Site C repressor site/domain ranges in length from about 1 to about 50 bases, usually from about 5 to about 45 bases.

In many embodiments, the target Site C site has a sequence found in a limited region of the human tert minimal promoter, where this limited region typically ranges from about −40 to about −90, usually from about 45 to about −85 and more usually from about −45 to about −80 relative to the "A" of the telomerase ATG codon.

Of particular interest in certain embodiments is a nucleic acid having a sequence found in SEQ ID NO:01 (e.g., a sequence range of at least about 2, usually at least about 5 and often at least about 10, 20, 25, 30 or more bases up to about 45 to 50 bases, where, in certain embodiments, the target Site C domain will have a sequence that is identical to a sequence of SEQ ID NO:01. SEQ ID NO:01 has the following sequence:

GGCCCCGCCCTCTCCTCGCGGCGC-
GAGTTTCAGGCAGCGCT (SEQ ID NO:01)

In certain embodiments, the target Site C site includes the sequence of −69 to −57 of the human TERT minimal promoter. In other words, the sequence of the Site C site is:

GGCGCGAGTTTCA (SEQ ID NO:02).

In certain embodiments, the target Site C site includes the sequence of −67 to −58 of the human TERT minimal promoter. In other words, the sequence of the Site C site is:

CGCGAGTTTC (SEQ ID NO:03).

In certain embodiments, the target Site C site includes the sequence of −69 to −49 of the human TERT minimal promoter. In other words, the sequence of the Site C site is:

GGCGCGAGTTTCAGGCAGCGC (SEQ ID NO:04).

Also of interest are Site C sites that have a sequence that is substantially the same as, or identical to, the Site C repressor binding site sequences as described above, e.g., SEQ ID NOs: 01 to 04. A given sequence is considered to be substantially similar to this particular sequence if it shares high sequence similarity with the above described specific sequences, e.g. at least 75% sequence identity, usually at least 90%, more usually at least 95% sequence identity with the above specific sequences. Sequence similarity is calculated based on a reference sequence, which may be a subset of a larger sequence. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings, i.e. parameters w=4 and T=17). Of particular interest in certain embodiments are nucleic acids of substantially the same length as the specific nucleic acid identified above, where by substantially the same length is meant that any difference in length does not exceed about 20 number %, usually does not exceed about 10 number % and more usually does not exceed about 5 number %; and have sequence identity to this sequence of at least about 90%, usually at least about 95% and more usually at least about 99% over the entire length of the nucleic acid. Also of interest are nucleic acids that represent a modified or altered Site C site, e.g., where the site includes one or more deletions or substitutions as compared to the above specific Site C sequences, including a deletion or substitution of a portion of the Site C repressor binding site, e.g., a deletion or substitution of at least one nucleotide.

Modulating TERT Expression

The subject invention provides methods of modulating, including both enhancing and repressing, TERT expression. As such, methods of both increasing and decreasing TERT expression are provided. In many embodiments, such methods are methods of modulating the binding interaction and resultant Site C TERT expression repression activity between a Site C site in a minimal TERT promoter and a Site C repressor protein, where in many embodiments the Site C repressor protein is a protein having an E2F DNA binding domain, particularly a Site C E2F DNA binding domain. As such, included are methods of either enhancing or inhibiting binding of Site C repressor protein to a TERT minimal promoter Site C site.

As indicated above, the Site C repressor protein whose interaction with the Site C repressor site is modulated in the subject methods is a protein that binds to the Site C repressor site and, in so binding, inhibits TERT expression. In many embodiments, the Site C repressor protein is a protein that binds to the Site C site via an E2F DNA binding domain present on the repressor protein, i.e., that is part of the repressor protein. In certain embodiments, the target Site C repressor proteins are proteins that include a DNA binding domain having a sequence of residues according to the following formula, where X is any residue:

$$R-(X)_{38}-R-R-X-Y$$

In certain embodiments, the target Site C repressor proteins are proteins that include a DNA binding domain that has an amino acid sequence that is at least homologous to the amino acid sequence of the DNA binding domain of either E2F-1 or E2F-4. The amino acid sequence of the DNA binding domain of E2F-1 is:

GRGRHPGKGVKSPGEKSRYETSLNLTT-
KRFLELLSHSADGVVDLNWMEVL KVQKRRIYDITNV-
LEGIQLIA KKSKNHIQWLGSH (SEQ ID NO:05).

The amino acid sequence of the DNA binding domain of E2F-4 is:

PPGTPSRHEKSLGLLTTKFVS-
LLQEAKDGVLDLKLAADTLAVRQKRRIYDITN VLE-
GIGLIEKKSKNSIQWK GVGP (SEQ ID NO:06).

By at least homologous is meant that the target Site C repressor protein has a DNA binding domain which includes an amino acid sequence that has at least 20%, usually at least 25% sequence identity with at least one of the specific E2F binding domains provided above, where sequence identity for this particular purpose is measured using the BLAST compare two sequences program available on the NCBI website using default settings.

As such, in certain embodiments, target repressor proteins are E2F proteins. Target E2F proteins of interest include, but are not limited to: E2F-1, E2F-2, E2F-3, E2F-4, E2F-5 and E2F-6; where in certain embodiments, E2F-6 is the target protein of interest. In yet other embodiments, the target Site C repressor protein is not an E2F protein, but is instead a protein that includes an E2F DNA binding site, as described above, or homologue thereof. In certain embodiments, the target Site C repressor protein acts in concert with one or more cofactors in binding to the Site C repressor site to inhibit the TERT transcription site. For example, in certain embodiments the Site C repressor protein's repressive activity upon binding to the Site C sequence is modulated by its interaction with one or more additional cofactors, in a manner analogous to the manner in which E2F's 1-5 are known to be converted from activators to repressors by binding to a cofactor from the Retinoblastoma (RB) family of proteins, including pRB, p107, or p130, as reviewed in: "The Regulation of E2F by pRB-Family proteins", N. Dyson; Genes Dev, 12, p 2245–62 (1998).

In modulating TERT expression, the interaction between the Site C repressor site and its repressor protein can be modified directly or indirectly. An example of direct modification of this interaction is where the binding of the repressor protein to the target sequence is modified by an agent that directly changes how the repressor protein binds to the Site C sequence, e.g., by occupying the DNA binding site of the repressor protein, by binding to the Site C sequence thereby preventing its binding to the repressor protein, etc. An example of indirect modification is modification/modulation of the Site C repressive activity via disruption of a binding interaction between the repressor protein and one or more cofactors (or further upstream in the chain of interactions, such as cofactors that interact with the Site C binding protein to make it either a repressor or activator, as described above) such that the repressive activity is modulated, by modification/alteration of the Site C DNA binding sequence such that binding to the repressor protein is modulated, etc.

Enhancing TERT Expression

Methods are provided for enhancing TERT expression. By enhancing TERT expression is meant that the expression level of the TERT coding sequence is increased by at least about 2 fold, usually by at least about 5 fold and sometimes by at least 25, 50, 100 fold and in particular about 300 fold or higher, as compared to a control, i.e., expression from an expression system that is not subjected to the methods of the present invention. Alternatively, in cases where expression of the TERT gene is so low that it is undetectable, expression of the TERT gene is considered to be enhanced if expression is increased to a level that is easily detectable.

In these methods, Site C repression of TERT expression is inhibited. By inhibited is meant that the repressive activity of the TERT Site C repressor binding site/repressor protein interaction with respect to TERT expression is decreased by a factor sufficient to at least provide for the desired enhanced level of TERT expression, as described above. Inhibition of Site C transcription repression may be accomplished in a number of ways, where representative protocols for inhibiting this TERT expression repression are now provided.

One representative method of inhibiting repression of transcription is to employ double-stranded, i.e., duplex, oligonucleotide decoys for the Site C repressor protein, which bind to the Site C repressor protein and thereby prevent the Site C repressor protein binding to its target Site C site in the TERT promoter, e.g., the Site C site of the TERT minimal promoter. These duplex oligonucleotide decoys have at least that portion of the sequence of the TERT Site C site required to bind to the Site C repressor protein and thereby prevent its binding to the Site C site. In many embodiments, the subject decoy nucleic acid molecules include a sequence of nucleotides that is the same as a sequence found in SEQ ID NOs: 01 to 04. In other embodiments, the subject decoy nucleic acid molecules include a sequence of nucleotides that is substantially the same as or identical to a sequence found in SEQ ID NOs: 01 to 04; where the terms substantially the same as and identical thereto in relation to nucleic acids are defined below. In many embodiments, the length of these duplex oligonucleotide decoys ranges from about 5 to about 5000, usually from about 5 to about 500 and more usually from about 10 to about 50 bases. In using such oligonucleotide decoys, the decoys are placed into the environment of the Site C site and its Site C repressor protein, resulting in de-repression of the transcription and expression of the TERT coding sequence. Oligonucleotide decoys and methods for their use and administration are further described in general terms in Morishita et al., Circ Res (1998) 82 (10):1023–8. These oligonucleotide decoys generally include a TERT Site C repressor binding site recognized by the target Site C repressor protein, including the specific regions detailed above, where these particular embodiments include nucleic acid compositions of the subject invention, as described in greater detail below.

Instead of the above described decoys, other agents that disrupt binding of the Site C repressor protein to the target TERT Site C repressor binding site and thereby inhibit its expression repression activity may be employed. Other agents of interest include, among other types of agents, small molecules that bind to the Site C repressor protein and inhibit its binding to the Site C repressor region. Alternatively, agents that bind to the Site C sequence and inhibit its binding to the Site C repressor protein are of interest. Alternatively, agents that disrupt Site C repressor protein—protein interactions with cofactors, e.g., cofactor binding, and thereby inhibit Site C repression are of interest.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below. Small molecule agents of particular interest include pyrrole-imidazole polyamides, analogous to those described in Dickinson et al., Biochemistry 1999 Aug 17;38(33):10801–7. Other agents include "designer" DNA binding proteins that bind Site C (without causing repression) and prevent the Site C repressor protein from binding.

In yet other embodiments, expression of the Site C repressor protein is inhibited. Inhibition of Site C repressor protein expression may be accomplished using any convenient means, including administration of an agent that inhibits Site C repressor expression (e.g., antisense agents), inactivation of the Site C repressor gene, e.g., through recombinant techniques, etc.

For example, where the Site C repressor protein is an E2F protein, e.g., E2F-6 or a homologue thereof, antisense molecules can be used to down-regulate expression of the target repressor protein in cells. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted repressor protein, and inhibits expression of the targeted repressor protein. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), Nature Biotechnol. 14:840–844).

A specific region or regions of the endogenous sense strand mRNA sequence is chosen to be complemented by the antisense sequence.

Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), Nucl. Acids Res. 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), Appl. Biochem. Biotechnol. 54:43–56.

In another embodiment, the Site C repressor protein gene is inactivated so that it no longer expresses a functional repressor protein. By inactivated is meant that the Site C repressor gene, e.g., coding sequence and/or regulatory elements thereof, is genetically modified so that it no longer expresses functional repressor protein. The alteration or mutation may take a number of different forms, e.g., through deletion of one or more nucleotide residues in the repressor region, through exchange of one or more nucleotide residues in the repressor region, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998,144; 5,948,653; 5,925,544; 5,830,698;

5,780,296; 5,776,744; 5,721,367; 5,614,396; 5,612,205; the disclosures of which are herein incorporated by reference.

The above described methods of enhancing TERT expression find use in a number of different applications. In many applications, the subject methods and compositions are employed to enhance TERT expression in a cell that endogenously comprises a TERT gene, e.g. for enhancing expression of hTERT in a normal human cell in which TERT expression is repressed. The target cell of these applications is, in many instances, a normal cell, e.g. a somatic cell. Expression of the TERT gene is considered to be enhanced if, consistent with the above description, expression is increased by at least about 2 fold, usually at least about 5 fold and often 25, 50, 100 fold, 300 fold or higher, as compared to a control, e.g., an otherwise identical cell not subjected to the subject methods, or becomes detectable from an initially undetectable state, as described above.

A more specific application in which the subject methods find use is to increase the proliferative capacity of a cell. The term "proliferative capacity" as used herein refers to the number of divisions that a cell can undergo, and preferably to the ability of the target cell to continue to divide where the daughter cells of such divisions are not transformed, i.e., they maintain normal response to growth and cell cycle regulation. The subject methods typically result in an increase in proliferative capacity of at least about 1.2–2 fold, usually at least about 5 fold and often at least about 10, 20, 50 fold or even higher, compared to a control. As such, yet another more specific application in which the subject methods find use is in the delay of the occurrence of cellular senescence. By practicing the subject methods, the onset of cellular senescence may be delayed by a factor of at least about 1.2–2 fold, usually at least about 5 fold and often at least about 10, 20, 50 fold or even higher, compared to a control.

Methods of Inhibiting TERT Expression

As mentioned above, also provided are methods for inhibiting TERT expression, e.g., by enhancing Site C repression of TERT expression and thereby inhibiting TERT expression. In such methods, the amount and/or activity of the Site C repressor protein is increased so as to enhance Site C repressor mediated repression of TERT expression. A variety of different protocols may be employed to achieve this result, including administration of an effective amount of the Site C repressor protein or analog/mimetic thereof, an agent that enhances expression of Site C repressor protein or an agent that enhances the activity of the Site C repressor protein.

As such, the nucleic acid compositions that encode the Site C repressor protein find use in situations where one wishes to enhance the activity of the repressor protein in a host. The repressor protein genes, gene fragments, or the encoded proteins or protein fragments are useful in gene therapy to treat disorders in which inhibition of TERT expression is desired, including those applications described in greater detail below. Expression vectors may be used to introduce the gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or protein may be introduced into tissues or host cells by any number of routes, including viral infection, microinjection, or fusion of vesicles. Jet injection may also be used for intramuscular administration, as described by Furth et al. (1992), Anal Biochem 205:365–368. The DNA may be coated onto gold microparticles, and delivered intradermally by a particle bombardment device, or "gene gun" as described in the literature (see, for example, Tang et al. (1992), Nature 356:152–154), where gold microprojectiles are coated with the DNA, then bombarded into skin cells.

Therapeutic Applications of TERT Expression Modulation

The methods find use in a variety of therapeutic applications in which it is desired to modulate, e.g., increase or decrease, TERT expression in a target cell or collection of cells, where the collection of cells may be a whole animal or portion thereof, e.g., tissue, organ, etc. As such, the target cell(s) may be a host animal or portion thereof, or may be a therapeutic cell (or cells) which is to be introduced into a multicellular organism, e.g., a cell employed in gene therapy. In such methods, an effective amount of an active agent that modulates TERT expression, e.g., enhances or decreases TERT expression as desired, is administered to the target cell or cells, e.g., by contacting the cells with the agent, by administering the agent to the animal, etc. By effective amount is meant a dosage sufficient to modulate TERT expression in the target cell(s), as desired.

In the subject methods, the active agent(s) may be administered to the targeted cells using any convenient means capable of resulting in the desired enhancement of TERT expression. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intratracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. oligonucleotide decoy, it may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

The subject methods find use in the treatment of a variety of different conditions in which the enhancement of TERT expression in the host is desired. By treatment is meant that at least an amelioration of the symptoms associated with the condition afflicting the host is achieved, where amelioration is used in a broad sense to refer to at least a reduction in the magnitude of a parameter, e.g. symptom (such as inflammation), associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

As indicated above, the subject invention provides methods of treating disease conditions resulting from a lack of TERT expression and methods of treating disease conditions resulting from unwanted TERT expression. Representative disease conditions for each category are now described in greater detail separately.

Treatment of Disease Conditions by Increasing TERT Expression

One representative disease condition that may be treated according to the subject invention is Progeria, or Hutchinson-Gilford syndrome. This condition is a disease of shortened telomeres for which no known cure exists. It afflicts children, who seldom live past their early twenties. In many ways progeria parallels aging itself. However, these children are born with short telomeres. Their telomeres don't shorten at a faster rate; they are just short to begin with. The subject methods can be used in such conditions to further delay natural telomeric shortening and/or increase telomeric length, thereby treating this condition.

Another specific disease condition in which the subject methods find use is in immune senescence. The effectiveness of the immune system decreases with age. Part of this decline is due to fewer T-lymphocytes in the system, a result of lost replicative capacity. Many of the remaining T-lymphocytes experience loss of function as their telomeres shorten and they approach senescence. The subject methods can be employed to inhibit immune senescence due to telomere loss. Because hosts with aging immune systems are at greater risk of developing pneumonia, cellulitis, influenza, and many other infections, the subject methods reduce morbidity and mortality due to infections.

The subject methods also find use in AIDS therapy. HIV, the virus that causes AIDS, invades white blood cells, particularly CD4 lymphocyte cells, and causes them to reproduce high numbers of the HIV virus, ultimately killing cells. In response to the loss of immune cells (typically about a billion per day), the body produces more CD8 cells to be able to suppress infection. This rapid cell division accelerates telomere shortening, ultimately hastening immune senescence of the CD8 cells. Anti-retroviral therapies have successfully restored the immune systems of AIDS patients, but survival depends upon the remaining fraction of the patient's aged T-cells. Once shortened, telomere length has not been naturally restored within cells. The subject methods can be employed to restore this length and/or prevent further shortening. As such the subject methods can spare telomeres and is useful in conjunction with the anti-retroviral treatments currently available for HIV.

Yet another type of disease condition in which the subject methods find use is cardiovascular disease. The subject methods can be employed to extend telomere length and replicative capacity of endothelial cells lining blood vessel walls (DeBono, Heart 80:110–1, 1998). Endothelial cells form the inner lining of blood vessels and divide and replace themselves in response to stress. Stresses include high blood pressure, excess cholesterol, inflammation, and flow stresses at forks in vessels. As endothelial cells age and can no longer divide sufficiently to replace lost cells, areas under the endothelial layer become exposed. Exposure of the underlying vessel wall increases inflammation, the growth of smooth muscle cells, and the deposition of cholesterol. As a result, the vessel narrows and becomes scarred and irregular, which contributes to even more stress on the vessel (Cooper, Cooke and Dzau, *J Gerontol Biol Sci* 49: 191–6, 1994). Aging endothelial cells also produce altered amounts of trophic factors (hormones that affect the activity of neighboring cells). These too contribute to increased clotting, proliferation of smooth muscle cells, invasion by white blood cells, accumulation of cholesterol, and other changes, many of which lead to plaque formation and clinical cardiovascular disease (Ibid.). By extending endothelial cell telomeres, the subject methods can be employed to combat the stresses contributing to vessel disease. Many heart attacks may be prevented if endothelial cells were enabled to continue to divide normally and better maintain cardiac vessels. The occurrence of strokes caused by the aging of brain blood vessels may also be significantly reduced by employing the subject methods to help endothelial cells in the brain blood vessels to continue to divide and perform their intended function.

The subject methods also find use in skin rejuvenation. The skin is the first line of defense of the immune system and shows the most visible signs of aging (West, Arch Dermatol 130(1):87–95, 1994). As skin ages, it thins, develops wrinkles, discolors, and heals poorly. Skin cells divide quickly in response to stress and trauma; but, over time, there are fewer and fewer actively dividing skin cells. Compounding the loss of replicative capacity in aging skin is a corresponding loss of support tissues. The number of blood vessels in the skin decreases with age, reducing the nutrients that reach the skin. Also, aged immune cells less effectively fight infection. Nerve cells have fewer branches, slowing the response to pain and increasing the chance of trauma. In aged skin, there are also fewer fat cells, increasing susceptibility to cold and temperature changes. Old skin cells respond more slowly and less accurately to external signals. They produce less vitamin D, collagen, and elastin, allowing the extracellular matrix to deteriorate. As skin thins and loses pigment with age, more ultraviolet light penetrates and damages skin. To repair the increasing ultraviolet damage, skin cells need to divide to replace damaged cells, but aged skin cells have shorter telomeres and are less capable of dividing (Fossel, REVERSING HUMAN AGING. William Morrow & Company, New York City, 1996).

By practicing the subject methods, e.g., via administration of an active agent topically, one can extend telomere length, and slow the downward spiral that skin experiences with age. Such a product not only helps protect a person against the impairments of aging skin; it also permits rejuvenated skin cells to restore youthful immune resistance and appearance. The subject methods can be used for both medical and cosmetic skin rejuvenation applications.

Yet another disease condition in which the subject methods find use in the treatment of osteoporosis. Two types of cells interplay in osteoporosis: osteoblasts make bone and osteoclasts destroy it. Normally, the two are in balance and maintain a constant turnover of highly structured bone. In youth, bones are resilient, harder to break, and heal quickly. In old age, bones are brittle, break easily, and heal slowly and often improperly. Bone loss has been postulated to occur because aged osteoblasts, having lost much of their replicative capacity, cannot continue to divide at the rate necessary to maintain balance (Hazzard et al. PRINCIPLES OF GERIATRIC MEDICINE AND GERONTOLOGY, 2d ed. McGraw-Hill, New York City, 1994). The subject methods can be employed to lengthen telomeres of osteoblast and osteoclast stem cells, thereby encouraging bone replacement and proper remodeling and reinforcement. The resultant stronger bone improves the quality of life for the many sufferers of osteoporosis and provides savings from fewer fracture treatments. The subject methods are generally part of a comprehensive treatment regime that also includes calcium, estrogen, and exercise.

Additional disease conditions in which the subject methods find use are described in WO 99/35243, the disclosures of which are herein incorporated by reference.

In addition to the above described methods, the subject methods can also be used to extend the lifetime of a mammal. By extend the lifetime is meant to increase the time during which the animal is alive, where the increase is generally at least 1%, usually at least 5% and more usually at least about 10%, as compared to a control.

As indicated above, instead of a multicellular animal, the target may be a cell or population of cells which are treated according to the subject methods and then introduced into a multicellular organism for therapeutic effect. For example, the subject methods may be employed in bone marrow transplants for the treatment of cancer and skin grafts for burn victims. In these cases, cells are isolated from a human donor and then cultured for transplantation back into human recipients. During the cell culturing, the cells normally age and senesce, decreasing their useful lifespans. Bone marrow cells, for instance, lose approximately 40% of their replicative capacity during culturing. This problem is aggravated when the cells are first genetically engineered (Decary, Mouly et al. Hum Gene Ther 7(11): 1347–50, 1996). In such cases, the therapeutic cells must be expanded from a single engineered cell. By the time there are sufficient cells for transplantation, the cells have undergone the equivalent of 50 years of aging (Decary, Mouly et al. Hum Gene Ther 8(12): 1429–38, 1997). Use of the subject methods spares the replicative capacity of bone marrow cells and skin cells during culturing and expansion and thus significantly improves the survival and effectiveness of bone marrow and skin cell transplants. Any transplantation technology requiring cell culturing can benefit from the subject methods, including ex vivo gene therapy applications in which cells are cultured outside of the animal and then administered to the animal, as described in U.S. Pat. Nos. 6,068,837; 6,027,488; 5,824,655; 5,821,235; 5,770,580; 5,756,283; 5,665,350; the disclosures of which are herein incorporated by reference.

Treatment of Disease Conditions by Decreasing TERT Expression

As summarized above, also provided are methods for enhancing repression of TERT expression, where by enhancement of TERT expression repression is meant a decrease in TERT expression by a factor of at least about 2 fold, usually at least about 5 fold and more usually at least about 10 fold, as compared to a control. Methods for enhancing Site C mediated repression of TERT expression find use in, among other applications, the treatment of cellular proliferative disease conditions, particularly abnormal cellular proliferative disease conditions, including, but not limited to, neoplastic disease conditions, e.g., cancer. In such applications, an effective amount of an active agent, e.g., a Site C repressor protein, analog or mimetic thereof, a vector encoding a Site C repressor protein or active fragment thereof, an agent that enhances endogenous Site C repressor activity, an agent that enhances expression of Site C repressor protein, etc., is administered to the subject in need thereof. Treatment is used broadly as defined above, e.g., to include at least an amelioration in one or more of the symptoms of the disease, as well as a complete cessation thereof, as well as a reversal and/or complete removal of the disease condition, e.g., cure. Methods of treating disease conditions resulting from unwanted TERT expression, such as cancer and other diseases characterized by the presence of unwanted cellular proliferation, are described in, for example, U.S. Pat. Nos. 5,645,986; 5,656,638; 5,703,116; 5,760,062; 5,767,278; 5,770,613; and 5,863,936; the disclosures of which are herein incorporated by reference.

Nucleic Acid Compositions

Also provided by the subject invention are nucleic acid compositions, where the compositions are present in other than their natural environment, e.g., are isolated, recombinant, etc., that include a Site C repressor binding site/domain/region, as described above. In other embodiments, the subject nucleic acids have a sequence that is substantially the same as, or identical to, the Site C repressor binding site sequences as described above, e.g., SEQ ID NOs: 01 to 04. A given sequence is considered to be substantially similar to this particular sequence if it shares high sequence similarity with the above described specific sequences, e.g. at least 75% sequence identity, usually at least 90%, more usually at least 95% sequence identity with the above specific sequences. Sequence similarity is calculated based on a reference sequence, which may be a subset of a larger sequence. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings, i.e. parameters w=4 and T=17). Of particular interest in certain embodiments are nucleic acids of substantially the same length as the specific nucleic acid identified above, where by substantially the same length is meant that any difference in length does not exceed about 20 number %, usually does not exceed about 10 number % and more usually does not exceed about 5 number %; and have sequence identity to this sequence of at least about 90%, usually at least about 95% and more usually at least about 99% over the entire length of the nucleic acid.

Also provided are nucleic acids that hybridize to the above described nucleic acid under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C in a solution: 50% formamide, 5×SSC (150 mM NaCl, 15 mM trisodium citrate), 50 mM sodium phosphate (pH7.6), 5×Denhardt's solution, 10% dextran sulfate, and 20 μg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

In many embodiments, the above described nucleic acid compositions include the Site C sequence/domain region but do not include the full sequence of the hTERT minimal promoter. In these embodiments, the subject nucleic acids include no more than about 90 number %, usually no more than about 80 number % and more usually no more than about 75 number %, where in many embodiments the subject nucleic acids include less than about 50 number %, sometimes less than about 40 number % and sometimes less than about 25 number % of the total sequence of the hTERT minimal promoter. In certain embodiments, the length of the subject nucleic acids ranges from about 5 to about 5000 bases, sometimes from about 10 to about 2500 bases and usually from about 10 to about 1000 bases, where in certain embodiments the length ranges from about 10 to about 500 bases, sometimes from about 10 to about 250 bases and sometimes from about 10 to about 100 bases, including from about 10 to about 50 bases.

The above described nucleic acid compositions find use in a variety of different applications, including the preparation of constructs, e.g., vectors, expression systems, etc., as described more fully below, the preparation of probes for the Site C repressor binding site sequence in non-human animals, i.e., non-human Site C repressor binding site homologs, and the like. Where the subject nucleic acids are employed as probes, a fragment of the provided nucleic acid may be used as a hybridization probe against a genomic library from the target organism of interest, where low stringency conditions are used. The probe may be a large or small fragment, generally ranging in length from about 10 to 100 nt, usually from about 15 to 50 nt. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided nucleic acid sequences bind to the provided sequences under stringent hybridization conditions. By using probes, particularly labeled probes of DNA sequences, one can isolate homologous or related sequences.

The subject nucleic acids are isolated and obtained in substantial purity, generally as other than an intact chromosome. As such, they are present in other than their naturally occurring environment. Usually, the DNA will be obtained substantially free of other nucleic acid sequences that do not include a Site C repressor binding site sequence or fragment thereof, generally being at least about 50%, usually at least about 90% pure and are typically "recombinant", i.e. flanked by one or more nucleotides with which it is not normally associated on a naturally occurring chromosome.

The subject nucleic acids may be produced using any convenient protocol, including synthetic protocols, e.g., those where the nucleic acid is synthesized by a sequential monomeric approach (e.g., via phosphoramidite chemistry); where subparts of the nucleic acid are so synthesized and then assembled or concatamerized into the final nucleic acid, and the like. Where the nucleic acid of interest has a sequence that occurs in nature, the nucleic acid may be retrieved, isolated, amplified etc., from a natural source using conventional molecular biology protocols.

Also provided are nucleic acid compositions that include a modified or altered Site C site, e.g., where the site includes one or more deletions or substitutions as compared to the above specific Site C sequences, including a deletion or substitution of all or portion of the Site C repressor binding site, e.g., preferably a deletion or substitution of at least one nucleotide, in certain embodiments at least four nucleotides within the region of nucleotides from about −40 to about −90, usually from about −45 to about −85 and more usually from about −45 to about −80 relative to the "A" of the telomerase ATG codon, including the specific regions specified above, and usually at least 7 nucleotides from this region, and preferably all nucleotides from this region. Additionally, such a deletion may extend further, for example to include the nucleotides from positions −74 to −58, or subsets thereof, with the exception being deletions that result in the presence of a site which in fact binds to the Site C repressor protein in a manner that enhances TERT expression. The subject nucleic acids of this embodiment that include a deletion (or substitution) in all or a portion of the Site C repressor site of the TERT promoter may be present in the genome of a cell or animal of interest, e.g., as a "knockout" deletion in a transgenic cell or animal, where the cell or animal initially has this region, or may be present in an isolated form. A "knockout" animal could be produced from an animal that originally has the subject Site C repressor site using the sequences flanking specific Site C regions described here and the basic "knockout" technology known to those skilled in the art e.g. see U.S. Pat. No. 5,464,764 to Capecchi.

Also provided are constructs comprising the subject nucleic acid compositions, e.g., those that include the Site C repressor binding site or those that include a deletion in the Site C repressor binding site, inserted into a vector, where such constructs may be used for a number of different applications, including propagation, screening, genome alteration, and the like, as described in greater detail below. Constructs made up of viral and non-viral vector sequences may be prepared and used, including plasmids, as desired. The choice of vector will depend on the particular application in which the nucleic acid is to be employed. Certain vectors are useful for amplifying and making large amounts of the desired DNA sequence. Other vectors are suitable for expression in cells in culture, e.g., for use in screening assays. Still other vectors are suitable for transfer and expression in cells in a whole animal or person. The choice of appropriate vector is well within the skill of the art. Many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example. Additional examples of nucleic acid compositions that include the Site C repressor binding site are polymers, e.g. a double stranded DNA molecules, that mimic the Site C repressor site as described above. Also of interest are antisense sequences which are sufficiently homologous to the Site C binding site, such that they are useful to block attachment of the repressor protein to the Site C repressor binding site.

Also provided are expression cassettes, vectors or systems that find use in, among other applications, screening for agents that modulate, e.g., inhibit or enhance the repressive activity of the region, as described in greater detail below; and/or to provide for expression of proteins under the control of the expression regulation mechanism of the TERT gene. By expression cassette or system is meant a nucleic acid that includes a sequence encoding a peptide or protein of interest, i.e., a coding sequence, operably linked to a promoter sequence, where by operably linked is meant that expression of the coding sequence is under the control of the promoter sequence. The expression systems and cassettes of the subject invention comprise a Site C repressor binding site/region operably linked to the promoter, where the promoter is, in many embodiments, a TERT promoter, such as the hTERT promoter. See e.g., the hTERT promoter sequence described in Cong et al., Hum. Mol. Genet. (1999) 8:137–142.

As indicated above, expression systems comprising the subject regions find use in applications where it is desired to control expression of a particular coding sequence using the TERT transcriptional mechanism. In such applications, the expression system further includes the coding sequence of interest operably linked to the TERT promoter/Site C repressor binding site elements. The expression system is then employed in an appropriate environment to provide expression or non-expression of the protein, as desired, e.g., in an environment in which telomerase is expressed, e.g., a Hela cell, or in an environment in which telomerase is not expressed, e.g., an MRC5 cell. Alternatively, the expression system may be used in an environment in which telomerase expression is inducible, e.g., by adding to the system an additional agent that turns on telomerase expression.

The above applications of the subject nucleic acid compositions are merely representative of the diverse applications in which the subject nucleic acid compositions find use.

Generation of Antibodies

Also provided are methods of generating antibodies, e.g., monoclonal antibodies. In one embodiment, the blocking or inhibition, either directly or indirectly as described above, of the Site C repressor site/Site C repressor interaction is used to immortalize cells in culture, e.g., by enhancing telomerase expression. Exemplary of cells that may be used for this purpose are non-transformed antibody producing cells, e.g. B cells and plasma cells which may be isolated and identified for their ability to produce a desired antibody using known technology as, for example, taught in U.S. Pat. No. 5,627,052. These cells may either secrete antibodies (antibody-secreting cells) or maintain antibodies on the surface of the cell without secretion into the cellular environment. Such cells have a limited lifespan in culture, and are usefully immortalized by upregulating expression of telomerase using the methods of the present invention.

Because the above described methods are methods of increasing expression of TERT and therefore increasing the proliferative capacity and/or delaying the onset of senescence in a cell, they find applications in the production of a range of reagents, typically cellular or animal reagents. For example, the subject methods may be employed to increase proliferation capacity, delay senescence and/or extend the lifetimes of cultured cells. Cultured cell populations having enhanced TERT expression are produced using any of the protocols as described above, including by contact with an agent that inhibits repressor region transcription repression and/or modification of the repressor region in a manner such that it no longer represses TERT coding sequence transcription, etc.

The subject methods find use in the generation of monoclonal antibodies. An antibody-forming cell may be identified among antibody-forming cells obtained from an animal which has either been immunized with a selected substance, or which has developed an immune response to an antigen as a result of disease. Animals may be immunized with a selected antigen using any of the techniques well known in the art suitable for generating an immune response. Antigens may include any substance to which an antibody may be made, including, among others, proteins, carbohydrates, inorganic or organic molecules, and transition state analogs that resemble intermediates in an enzymatic process. Suitable antigens include, among others, biologically active proteins, hormones, cytokines, and their cell surface receptors, bacterial or parasitic cell membrane or purified components thereof, and viral antigens.

As will be appreciated by one of ordinary skill in the art, antigens which are of low immunogenicity may be accompanied with an adjuvant or hapten in order to increase the immune response (for example, complete or incomplete Freund's adjuvant) or with a carrier such as keyhole limpet hemocyanin (KLH).

Procedures for immunizing animals are well known in the art. Briefly, animals are injected with the selected antigen against which it is desired to raise antibodies. The selected antigen may be accompanied by an adjuvant or hapten, as discussed above, in order to further increase the immune response. Usually the substance is injected into the peritoneal cavity, beneath the skin, or into the muscles or bloodstream. The injection is repeated at varying intervals and the immune response is usually monitored by detecting antibodies in the serum using an appropriate assay that detects the properties of the desired antibody. Large numbers of antibody-forming cells can be found in the spleen and lymph node of the immunized animal. Thus, once an immune response has been generated, the animal is sacrificed, the spleen and lymph nodes are removed, and a single cell suspension is prepared using techniques well known in the art.

Antibody-forming cells may also be obtained from a subject which has generated the cells during the course of a selected disease. For instance, antibody-forming cells from a human with a disease of unknown cause, such as rheumatoid arthritis, may be obtained and used in an effort to identify antibodies which have an effect on the disease process or which may lead to identification of an etiological agent or body component that is involved in the cause of the disease. Similarly, antibody-forming cells may be obtained from subjects with disease due to known etiological agents such as malaria or AIDS. These antibody forming cells may be derived from the blood or lymph nodes, as well as from other diseased or normal tissues. Antibody-forming cells may be prepared from blood collected with an anticoagulant such as heparin or EDTA. The antibody-forming cells may be further separated from erythrocytes and polymorphs using standard procedures such as centrifugation with Ficoll-Hypaque (Pharmacia, Uppsula, Sweden). Antibody-forming cells may also be prepared from solid tissues such as lymph nodes or tumors by dissociation with enzymes such as collagenase and trypsin in the presence of EDTA.

Antibody-forming cells may also be obtained by culture techniques such as in vitro immunization. Briefly, a source of antibody-forming cells, such as a suspension of spleen or lymph node cells, or peripheral blood mononuclear cells are cultured in medium such as RPMI 1640 with 10% fetal bovine serum and a source of the substance against which it is desired to develop antibodies. This medium may be additionally supplemented with amounts of substances known to enhance antibody-forming cell activation and proliferation such as lipopolysaccharide or its derivatives or other bacterial adjuvants or cytokines such as IL-1, IL-2, IL-4, IL-5, IL-6, GM-CSF, and IFN-gamma. To enhance immunogenicity, the selected antigen may be coupled to the surface of cells, for example, spleen cells, by conventional techniques such as the use of biotin/avidin as described below.

Antibody-forming cells may be enriched by methods based upon the size or density of the antibody-forming cells relative to other cells. Gradients of varying density of solutions of bovine serum albumin can also be used to separate cells according to density. The fraction that is most enriched for desired antibody-forming cells can be determined in a preliminary procedure using the appropriate indicator system in order to establish the antibody-forming cells.

The identification and culture of antibody producing cells of interest is followed by enhancement of TERT expression in these cells by the subject methods, thereby avoiding the need for the immortalization/fusing step employed in traditional hybridoma manufacture protocols. In such methods, the first step is immunization of the host animal with an immunogen, typically a polypeptide, where the polypeptide will preferably be in substantially pure form, comprising less than about 1% contaminant. The immunogen may comprise the complete protein, fragments or derivatives thereof. To increase the immune response of the host animal, the protein may be combined with an adjuvant, where suitable adjuvants include alum, dextran sulfate, large polymeric anions, oil & water emulsions, e.g. Freundz's adjuvant, Freund's complete adjuvant, and the like. The protein may also be conjugated to synthetic carrier proteins or synthetic antigens. A variety of hosts may be immunized to produce the subject antibodies. Such hosts include rabbits, guinea pigs, rodents (e.g. mice, rats), sheep, goats, and the like. The protein is administered to the host, usually intradermally, with an initial dosage followed by one or more, usually at least two, additional booster dosages. Following immunization, generally, the spleen and/or lymph nodes of an immunized host animal provide a source of plasma cells. The plasma cells are treated according to the subject invention to enhance TERT expression and thereby, increase the proliferative capacity and/or delay senescence to produce "pseudo" immortalized cells. Culture supernatant from individual cells is then screened using standard techniques to identify those producing antibodies with the desired specificity. Suitable animals for production of monoclonal antibodies to a human protein include mouse, rat, hamster, etc. To raise antibodies against the mouse protein, the animal will generally be a hamster, guinea pig, rabbit, etc. The antibody may be purified from the cell supernatants or ascites fluid by conventional techniques, e.g. affinity chromatography using RFLAT-1protein bound to an insoluble support, protein A sepharose, etc.

In an analogous fashion, the subject methods are employed to enhance TERT expression in non-human animals, e.g., non-human animals employed in laboratory research. Using the subject methods with such animals can provide a number of advantages, including extending the lifetime of difficult and/or expensive to produce transgenic animals. As with the above described cells and cultures thereof, the expression of TERT in the target animals may be enhanced using a number of different protocols, including the administration of an agent that inhibits Site C repressor protein repression and/or targeted disruption of the Site C repressor binding site. The subject methods may be used with a number of different types of animals, where animals of particular interest include mammals, e.g., rodents such as mice and rats, cats, dogs, sheep, rabbits, pigs, cows, horses, and non-human primates, e.g. monkeys, baboons, etc.

Screening Assays

Also provided by the subject invention are screening protocols and assays for identifying agents that modulate, e.g., inhibit or enhance, Site C repression of TERT transcription. The screening methods include assays that provide for qualitative/quantitative measurements of TERT promoter controlled expression, e.g., of a coding sequence for a marker or reporter gene, in the presence of a particular candidate therapeutic agent. Assays of interest include assays that measures the TERT promoter controlled expression of a reporter gene (i.e. coding sequence, e.g., luciferase, SEAP, etc.) in the presence and absence of a candidate inhibitor agent, e.g., the expression of the reporter gene in the presence or absence of a candidate agent. The screening method may be an in vitro or in vivo format, where both formats are readily developed by those of skill in the art. Whether the format is in vivo or in vitro, an expression system, e.g., a plasmid, that includes a Site C repressor binding site, a TERT promoter and a reporter coding sequence all operably linked is combined with the candidate agent in an environment in which, in the absence of the candidate agent, the TERT promoter is repressed, e.g., in the presence of the Site C repressor protein that interacts with the Site C repressor binding site and causes TERT promoter repression. The conditions may be set up in vitro by combining the various required components in an aqueous medium, or the assay may be carried out in vivo, e.g., in a cell that normally lacks telomerase activity, e.g., an MRC5 cell, etc.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays that inhibit Site C repression of TERT transcription find use in the methods described above, e.g., in the enhancement of TERT expression. Alternatively, agents identified in the above screening assays that enhance Site C repression find use in applications where inhibition of TERT expression is desired, e.g., in the treatment of disease conditions characterized by the presence of unwanted TERT expression, such as cancer and other diseases characterized by the presence of unwanted cellular proliferation, where such methods are described in, for example, U.S. Pat. Nos. 5,645,986; 5,656,638; 5,703,116; 5,760,062; 5,767,278; 5,770,613; and 5,863,936; the disclosures of which are herein incorporated by reference.

The following examples are offered by way of illustration and not by way of limitation.

Experimental

I. Deletion Experiments 118 deletions of the minimal telomerase promoter as shown in FIG. 1 were constructed (using site specific in vitro mutagenesis as described in U.S. Pat. No. 5,702,931; the disclosure of which is herein incorporated by reference) to find regions within the telomerase promoter that contain potential repressor sites. These deletions ranged in size from 10 to 300 bases. Each deletion version of the minimal promoter was tested for its ability to express SEAP in MRC5 and HELA. Several of the deletions, all mapping about 50–100 bases upstream of the telomerase translation initiation codon (ATG), showed ~10 fold increased expression. The region was called the Site C region. The highest expression in MRC5 was obtained with the deletion called 11 K. This 30 base deletion includes bases −48 to −77 relative to the translation initiation codon ATG. However, a similar deletion, called 12K, that includes bases 48 to −57 results in 500 fold less expression. On the other hand, when 11 K and 12K were compared in HELA, they both gave equivalent amounts of expression. The repressor site in the Site C region therefore is contained, or overlaps with, the 20 bases present in 12K and absent in 11 K (i.e. −58 to −77).

To identify more specifically the bases that make up this repressor site, additional deletions were made. Each deletion is 10 bases long with 7 to 8 base overlaps between consecutive deletions. The deletions were made in the minimal telomerase promoter in the plasmid designated pSS120 (the full annotated sequence of pSSI20 is provided in FIG. 2). Each deletion mutant was independently made three times and all deletions were transiently transfected into MRC5 (telomerase negative normal cells) and HELA (telomerase positive immortal cells).

A portion of the 5' untranslated region is shown below, from −77 to 1, the start of translation. The repressor site extends from −77 to −48, as shown.

(SEQ ID NO.:7)
CTCCTCGC GGCGCGAGTT TCAGGCAGCG CTGCGTCCTG CTGCGCACGT GGGAAGCCCT repressor site (−77 to −48)

GGCCCCGGCC ACCCCGCGA
                 □
                 start codon (1)

Of particular interest are sequences with a deletion extending from −67 to −58, comprising the nucleotides CGCGAGTTTC (SEQ ID NO:03).

The expression levels were measured using the Secreted Alkaline Phosphatase Assay (SEAP Assay) commercially available from Clontech (Palo Alto, Calif.). The results are shown below.

II. Identification of E2F Consensus Sequence

The Site C region described above was analyzed for the presence of consensus sequences and an E2F transcription factor binding site consensus sequence (E2F-Q6) was identified (see below) utilizing software and databases provided by Genomatix (http://genomatix.gsf.de). This identified consensus sequence is located at −68 to −58 of the TERT promoter, or:

(SEQ ID NO:7)
CTCCTCGC GGCGCGAGTT TCAGGCAGCG CTGCGTCCTG CTGCGCACGT GGGAAGCCCT repressor site (−68 to −58)

GGCCCCGGCC ACCCCGCGA
|
start codon (1)

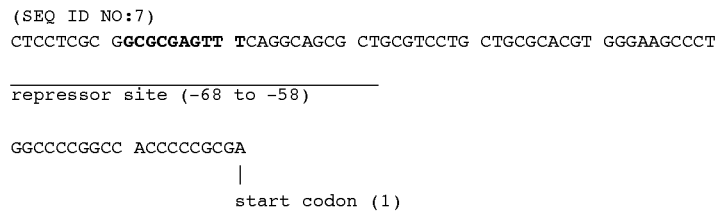

| Deletion | MRC5 | HELA |
|---|---|---|
| NONE (control) | 0.1931 | 78.3076 |
| −104 to −95 | 0.19 | 78.30 |
| −102 to −93 | 4.92 | 73.97 |
| −99 to −90 | 1.19 | 86.95 |
| −97 to −88 | 1.69 | 97.94 |
| −94 to −85 | 8.06 | 89.6 |
| −92 to −83 | 7.89 | 89.86 |
| −89 to −80 | 12.00 | 93.91 |
| −87 to −78 | 7.26 | 59.74 |
| −84 to −75 | 7.77 | 85.48 |
| −82 to −73 | 4.83 | 99.4 |
| −79 to −70 | 3.79 | 73.34 |
| −77 to −68 | 17.15 | 82.26 |
| −74 to −65 | 34.44 | 78.99 |
| −72 to −63 | 33.22 | 123.8 |
| −69 to −60 | 33.15 | 133.56 |
| −67 to −58 | 56.98 | 97.74 |
| −64 to −55 | 21.82 | 127.32 |
| −62 to −53 | 4.60 | 108 |
| −59 to −50 | 19.58 | 103.1 |

The column of deletions indicates the bases that were deleted in the repressor site, which is indicated relative to the AUG start codon. The columns for MRC5 and HELA show the level of expression observed for each deletion, reported as a percentage of the SV40 early promoter, which was used to normalize the two cell lines.

The data demonstrate that the deletion from "−67 to −58" gave a reading of 56.9852, as compared to a reading of 0.193109 in the control cells with no deletion in the promoter, giving an increase of 295 fold higher expression. This same deletion gave only 97.746 in HELA cells, compared to the undeleted control value of 78.3076, resulting in a 1.25 fold higher expression. This indicates that a repressor function operates in MRC5 cells to repress expression of the wild type telomerase promoter. When the expression level of deletion "−67 to −58" in MRC5 is compared to the wild type promoter in HELA it is observed that the deletion resulted in almost as much expression as the levels observed in HELA that are sufficient to maintain telomere length. That is, the expression of the deletion in MRC5 was 59.9852/78.3076= 77% of the wild type in HELA. This indicates that depressing the repressor in MRC5 allows for sufficient amounts of telomerase expression to maintain the length of the telomeres in the cells during cell division, and to stop cellular aging in these cells.

The identified consensus sequence, E2F-Q6, includes all of above described −67 to −58 deletion plus one base upstream. As can be seen from the above results, every deletion that overlaps this −67 to −58 site causes an elevation in expression with maximum expression occurring from the deletion of bases −67 to −58. The only exception to this general rule is the deletion from −62 to −53. This deletion actually, accidentally, creates a new sequence that matches the consensus E2F-Q6 sequence better than the original −67 to −58 site does.

III. Fine Mapping of the Site C Site

A "fine mapping" analysis of the Site C binding site was completed to determine the effect of each base within site C on telomerase repression and the results are tabulated below and shown graphically in FIG. 3. The "fine mapping" analysis involved single base mutations or deletions within Site C and assayed for their affects on the TERT promoter's ability to drive the expression of the SEAP reporter gene in transient transfection assays. In the graph of FIG. 3 the letters on the X-axis labeled "before" are the bases of Site C before mutagenesis. The letters labeled "after" are what the bases were changed to by in vitro mutagenesis. In this experiment only one base was changed at a time. That is, in one plasmid the C at −70 was changed to an A. That was the only change that took place in the plasmid. In another plasmid A at −63 was changed to a T. Again, that was the only change that took place in the plasmid. Each plasmid was then transiently transfected into MRC5 cells and expression of SEAP was assayed. The first data point shows the expression of SEAP under control of the wild type telomerase minimal promoter. This shows almost zero (83.10 SEAP units) expression. The next data point shows SEAP expression when the entire 10 base Site C sequence (SEQ ID NO. 03) is deleted. All the subsequent data points show the expression resulting from each of the single base changes shown in the X-axis.

This analysis resulted in the identification of the specific bases within site C that control the regulation of the telomerase promoter. Bases within the site C repressor binding site which were found to be influential in telomerase repression are shown in the site C sequence below as capital letters while those bases when mutated or deleted had little or no effect on telomerase repression are shown in small case.

Site C "fine mapping" results—CGCGagtTTc SEQ ID NO. 08 These results also show that the sequence that the Site C binding protein binds to is GGCGCGAGTTTCA (SEQ ID NO:02).

| Plasmid | Base # | Mutation | SEAP |
|---------|--------|----------|------|
| pSSI20  |        | Wild Type | 83.10 |
| pSSI304 |        | −67 to −58 deleted | 3093.70 |
| pSSI658 | −72    | G −> C   | 268.37 |
| pSSI663 | −71    | A −> G   | 208.63 |
| pSSI664 | −70    | A −> C   | 256.93 |
| pSSI667 | −69    | C −> G   | 596.70 |
| pSSI552 | −68    | C −> G   | 879.20 |
| pSSI645 | −67    | G −> C   | 1841.70 |
| pSSI670 | −66    | C −> G   | 3021.37 |
| pSSI673 | −65    | A −> C   | 3274.37 |
| pSSI677 | −64    | A −> G   | 2115.03 |
| pSSI679 | −63    | T −> A   | 968.70 |
| pSSI682 | −62    | C −> G   | 542.80 |
| pSSI686 | −61    | C −> T   | 1286.37 |
| pSSI688 | −60    | C −> T   | 2032.37 |
| pSSI691 | −59    | A −> T   | 2005.03 |
| pSSI694 | −58    | A −> C   | 1328.70 |
| pSSI697 | −57    | T −> A   | 1047.03 |
| pSSI700 | −56    | A −> G   | 66.27 |
| pSSI703 | −55    | A −> G   | 185.03 |
| pSSI706 | −54    | G −> C   | 369.03 |
| pSSI710 | −53    | G −> A   | 237.70 |

IV. Gel Shift Characterization of the Site C Site

The following oligos (each one was made double stranded) were employed in gel shift experiments using nuclear extracts from the normal cell line IMR90 and the immortal cell line Raji (Nuclear extracts of IMR90, Catalog #1012217, and Raji, Catalog #100156 were purchased from Geneka Biotechnology Inc.). IMR90 cells can be obtained from ATCC Catalog #CCL-186. Raji cells can be obtained from ATCC Catalog #CCL-86.). The gel shift protocol that was followed is from the BandShift Kit, Amersham Pharmacia Biotech, XY-026-00-06. The following changes to their protocol were made: the binding reaction is at 4C for 1 hour and no loading dye is added prior to electrophoresis. The results were identical for IMR90 and Raji. The ability of each oligo to shift in a gel shift assay, using either nuclear extract, when radioactively labeled are shown below. oligo The following mutant gel shift oligo (double stranded) in which base −65 (relative to the ATG of telomerase) was converted from a C to an A (shown in green) was also assayed.

TCTCCTCGCGGCGAGAGTTTCAGGCAGCGC (SEQ ID NO:23)

Previous SEAP assays (See Experiment "III. Fine Mapping of the Site C Site" above) had shown that this mutation abolished repressor binding as much as the complete deletion of the original 10 base site C sequence (SEQ ID NO:03). This mutant oligo did not cause a shift, indicating that the gel shift data agrees with the expression data.

As such, the following sequence is another Site C sequence:

GGCGCGAGTTTCAGGCAGCGC (SEQ ID NO:04)

It is evident from the above results and discussion that the subject invention provides important new nucleic acid compositions that find use in a variety of applications, including the establishment of expression systems that exploit the regulatory mechanism of the TERT gene and the establishment of screening assays for agents that enhance TERT expression. In addition, the subject invention provides methods of enhancing TERT expression in a cellular or animal host, which methods find use in a variety of applications, including the production of scientific research reagents and therapeutic treatment applications. Accordingly, the subject invention represents significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of

| Oligo Name | Result | Sequence | |
|------------|--------|----------|---|
| SSI586 | No Shift | TCTCCTCGCGGCGCGAGTTTCAGG | (SEQ ID NO:09) |
| SSI584 | No Shift | TCTCCTCGCGGCGCGAGTTTCAGGCA | (SEQ ID NO:10) |
| SSI582 | No Shift | TCTCCTCGCGGCGCGAGTTTCAGGCAGC | (SEQ ID NO:11) |
| SSI614 | Weak Shift | TCTCCTCGCGGCGCGAGTTTCAGGCAGCG | (SEQ ID NO:12) |
| SSI570 | Strong Shif | TCTCCTCGCGGCGCGAGTTTCAGGCAGCGC | (SEQ ID NO:13) |
| SSI630 | Strong Shift | CTCGCGGCGCGAGTTTCAGGCAGCGCTG | (SEQ ID NO:14) |
| SSI570 | Strong Shift | TCTCCTCGCGGCGCGAGTTTCAGGCAGCGC | (SEQ ID NO:15) |
| SSI572 | Strong Shift | TCCTCGCGGCGCGAGTTTCAGGCAGCGC | (SEQ ID NO:16) |
| SSI574 | Strong Shift | CTCGCGGCGCGAGTTTCAGGCAGCGC | (SEQ ID NO:17) |
| SSI634 | Strong Shift | CGCGGCGCGAGTTTCAGGCAGCGCTGCGTC | (SEQ ID NO:18) |
| SSI636 | Strong Shift | CGGCGCGAGTTTCAGGCAGCGCTGCGTC | (SEQ ID NO:19) |
| SSI638 | Weak Shift | GCGCGAGTTTCAGGCAGCGCTGCGTC | (SEQ ID NO:20) |
| SSI640 | Weak Shift | CGCGAGTTTCAGGCAGCGCTGCGTC | (SEQ ID NO:21) |
| SSI642 | Weak Shift | GCGAGTTTCAGGCAGCGCTGCGTC | (SEQ ID NO:22) | ordinary skill in the art in light of the teachings of this invention that certain changes and modifications may be made thereto without departing from the spirit or scope of the appended claims.

What is claimed is:

1. An in vitro method of determining whether an agent inhibits Site C repression of Telomerase Reverse Transcriptase (TERT) transcription, said method comprising:
   (a) contacting said agent with an expression system comprising a Site C repressor binding site and a coding sequence operably linked to a TERT promoter under conditions such that in the absence of said agent transcription of said coding sequence is repressed;
   (b) determining whether transcription of said coding sequence is repressed in the presence of said agent; and
   (c) identifying said agent as an agent that inhibits Site C repression of TERT transcription if transcription of said coding sequence is not repressed in the presence of said agent.

2. The method according to claim 1, wherein said contacting step occurs in a cell-free environment.

3. The method according to claim 1, wherein said contacting step occurs in a cell.

4. The method according to claim 1, wherein said agent is a small molecule.

5. The method according to claim 1, wherein said Site C repressor binding site comprises the sequence selected from the group consisting of SEQ ID NOs: 01 to 04.

6. The method according to claim 5, wherein said Site C repressor binding site comprises the sequence of SEQ ID NO:01.

7. The method according to claim 5, wherein said Site C repressor binding site comprises the sequence of SEQ ID NO:02.

8. The method according to claim 5, wherein said Site C repressor binding site comprises the sequence of SEQ ID NO:03.

9. The method according to claim 5, wherein said Site C repressor binding site comprises the sequence of SEQ ID NO:04.

10. The method according to claim 1, wherein said expression system is present inside of a cell.

11. The method according to claim 1, wherein said expression system is present in a cell free environment.

12. An in vitro method of determining whether an agent inhibits Site C repression of Telomerase Reverse Transcriptase (TERT) transcription, said method comprising:
  (a) contacting said agent with an expression system comprising a Site C repressor binding site and a coding sequence operably linked to a TERT promoter, wherein said expression system is present inside of a cell and said contacting is under conditions such that in the absence of said agent transcription of said coding sequence is repressed;
  (b) determining whether transcription of said coding sequence is repressed in the presence of said agent; and
  (c) identifying said agent as an agent that inhibits Site C repression of TERT transcription if transcription of said coding sequence is not repressed in the presence of said agent.

13. The method according to claim 12, wherein said Site C repressor binding site comprises the sequence selected from the group consisting of SEQ ID NOs: 01 to 04.

14. The method according to claim 13, wherein said Site C repressor binding site comprises the sequence selected from the group consisting of SEQ ID NO:01.

15. The method according to claim 13, wherein said Site C repressor binding site comprises the sequence selected from the group consisting of SEQ ID NO:02.

16. The method according to claim 13, wherein said Site C repressor binding site comprises the sequence selected from the group consisting of SEQ ID NO:03.

17. The method according to claim 13, wherein said Site C repressor binding site comprises the sequence selected from the group consisting of SEQ ID NO:04.

* * * * *

UNITED STATES PATENT AND TRADEMARK OFFICE
CERTIFICATE OF CORRECTION

PATENT NO. : 6,686,159 B2
DATED : February 3, 2004
INVENTOR(S) : Andrews, William H. et al.

It is certified that error appears in the above-identified patent and that said Letters Patent is hereby corrected as shown below:

Column 25,
In the table under Mutation column, line 12, it should read:
-- C-> A --

Column 26,
Line 3, where it is stated "converted from a C to an A (shown in green) was also assayed.

Signed and Sealed this

Third Day of May, 2005

JON W. DUDAS
*Director of the United States Patent and Trademark Office*